US012751824B2

(12) United States Patent
McNiven et al.

(10) Patent No.: US 12,751,824 B2
(45) Date of Patent: Oct. 6, 2026

(54) ROTATIONAL DETACHABLE OUTER CATHETER

(71) Applicant: Cephea Valve Technologies, Inc., Abbott Park, IL (US)

(72) Inventors: Sean A. McNiven, Menlo Park, CA (US); Randolf Von Oepen, Aptos, CA (US); Austin Sherman, Sunnyvale, CA (US); Francisco Valencia, East Palo Alto, CA (US)

(73) Assignee: Cephea Valve Technologies, Inc., Abbott Park, IL (US)

( * ) Notice: Subject to any disclaimer, the term of this patent is extended or adjusted under 35 U.S.C. 154(b) by 428 days.

(21) Appl. No.: 18/516,000

(22) Filed: Nov. 21, 2023

(65) Prior Publication Data

US 2024/0173130 A1 May 30, 2024

Related U.S. Application Data

(60) Provisional application No. 63/385,296, filed on Nov. 29, 2022.

(51) Int. Cl.

| | |
|---|---|
| ***A61F 2/24*** | (2006.01) |
| ***A61M 25/01*** | (2006.01) |
| *A61F 2/95* | (2013.01) |

(52) U.S. Cl.

CPC .......... *A61F 2/2436* (2013.01); *A61F 2/2427* (2013.01); *A61F 2/9517* (2020.05); *A61M 25/0136* (2013.01)

(58) Field of Classification Search

CPC .... A61F 2/2427; A61F 2/2436; A61F 2/9517; A61M 25/0136; A61M 2025/0004; A61M 25/0097; A61M 2025/0681

See application file for complete search history.

(56) References Cited

U.S. PATENT DOCUMENTS

| | | | | |
|---|---|---|---|---|
| 7,736,388 | B2 | 6/2010 | Goldfarb | |
| 8,870,948 | B1 | 10/2014 | Erzberger | |
| 10,470,881 | B2 | 11/2019 | Noe | |
| 2002/0161389 | A1* | 10/2002 | Boyle | A61F 2/013 606/200 |
| 2005/0107739 | A1* | 5/2005 | Palma | A61M 39/1011 604/104 |
| 2016/0158000 | A1 | 6/2016 | Granada | |
| 2018/0028177 | A1 | 2/2018 | Van Oepen | |
| 2018/0028314 | A1* | 2/2018 | Ekvall | A61F 2/2412 |

(Continued)

FOREIGN PATENT DOCUMENTS

| | | |
|---|---|---|
| WO | 2016183526 | 11/2016 |
| WO | 2023015133 | 2/2023 |

*Primary Examiner* — Javier G Blanco

(74) *Attorney, Agent, or Firm* — SLEMAN & LUND LLP

(57) ABSTRACT

A delivery system for delivering an implantable medical device, such as a prosthetic heart valve, intravascularly to a target site, such as a heart valve annulus in a patient. The system includes an outer sheath, a connecting arm connected to the outer sheath, a valve cover at the distal end of the outer sheath and a steering catheter within the outer sheath. A handle is connected to the steering catheter so that rotation of the handle rotates the steering catheter. A coupling mechanism has a first condition rotationally coupling the outer sheath to the steering catheter, and a second condition in which the outer sheath is rotationally uncouple from the steering catheter.

11 Claims, 32 Drawing Sheets

(56) References Cited

U.S. PATENT DOCUMENTS

| | | | | |
|---|---|---|---|---|
| 2018/0028779 | A1* | 2/2018 | von Oepen | A61F 2/2427 |
| 2018/0092744 | A1 | 4/2018 | Von Oepen | |
| 2020/0155803 | A1 | 5/2020 | Caton | |
| 2020/0155804 | A1 | 5/2020 | Von Oepen | |
| 2020/0323634 | A1 | 10/2020 | Von Oepen | |

* cited by examiner

ROTATIONAL DETACHABLE OUTER CATHETER

CROSS-REFERENCE TO RELATED APPLICATIONS

The present application claims the benefit of the filing date of U.S. Provisional Patent Application No. 63/385,296 filed Nov. 29, 2022, the disclosure of which is hereby incorporated herein by reference.

BACKGROUND OF THE INVENTION

The present disclosure relates generally to devices, systems and methods for delivering an interventional device into a patient for implantation. More particularly, the present disclosure relates to devices, systems and methods for transseptal delivery of a collapsible prosthetic heart valve to a native mitral valve annulus, and to the deployment of the prosthetic heart valve at the native mitral valve annulus.

Interventional medical devices that are collapsible to a relatively small circumferential size can be delivered into a patient less invasively than devices that are not collapsible. For example, a collapsible prosthetic heart valve may be delivered into a patient via a tube-like delivery apparatus such as a catheter, a trocar, a laparoscopic instrument, or the like. This collapsibility can avoid the need for a more invasive procedure such as full open-chest, open-heart surgery, thereby reducing the risks, costs and time associated with an open-heart surgical procedure.

Collapsible prosthetic heart valves typically take the form of a valve structure mounted on a stent. There are two types of stents on which the valve structures are ordinarily mounted: a self-expanding stent and a balloon-expandable stent. Valves with self-expanding stents generally are first collapsed or crimped to reduce their circumferential size, and then loaded into a delivery apparatus. Valves with balloon-expandable stents generally are crimped around a deflated balloon that is mounted to a delivery apparatus.

When a collapsed prosthetic valve has reached the desired implantation site in the patient (e.g., at or near the annulus of the patient's heart valve that is to be replaced by the prosthetic valve), the prosthetic valve can be deployed or released from the delivery apparatus. For balloon-expandable valves, this generally involves assuring the proper location of the valve, and then expanding the balloon positioned within the valve stent. For self-expanding valves, on the other hand, the stent automatically expands as the sheath covering the valve is withdrawn.

There are many considerations in properly deploying a prosthetic heart valve in the native valve annulus. The prosthetic valve should be placed at the same or very nearly the same angle as the native valve. A valve that is off axis could cause turbulent blood flow and/or potential paravalvular leaks. The prosthetic valve also should be implanted so that its center aligns with the center of the native valve. Off-center deployment or implantation of the prosthetic valve could interfere with neighboring valves or the heart's conduction system. Additionally, the prosthetic heart valve should be implanted at the proper depth within the native valve annulus, also so as to not interfere with the heart's conduction system.

A safe, accurate and efficient delivery system and method for a prosthetic heart valve that addresses some or all of the foregoing concerns is described herein. During use of the described system to deploy a prosthetic mitral valve, it may become necessary to reposition the partially deployed valve so that it abuts the ventricular side of the native mitral valve annulus. Also described herein are features of the delivery system that facilitate such repositioning.

BRIEF SUMMARY OF THE INVENTION

One embodiment of a delivery system for delivering a prosthetic heart valve to a targeted anatomical site within a patient includes a catheter assembly including an outer sheath extending in a longitudinal direction between a proximal end and a distal end; a connecting arm connected to the outer sheath at the proximal end, the connecting arm extending away from the outer sheath in a direction transverse to the longitudinal direction; a valve cover at the distal end of the outer sheath, the valve cover having a proximal end, a distal end, and a size and a shape for housing the medical device in a collapsed condition; and a steering catheter coaxially arranged within the outer sheath, the steering catheter having a longitudinal axis and a flexible distal portion capable of deflecting in multiple directions relative to the longitudinal axis, wherein deflection of the distal portion of the steering catheter causes a corresponding deflection of a distal portion of the outer sheath; a handle connected to the steering catheter such that rotation of the handle causes a corresponding rotation of the steering catheter about the longitudinal axis; and a coupling mechanism having a first condition in which the outer sheath is rotationally coupled to the steering catheter so that rotation of the steering catheter about the longitudinal axis results in a corresponding rotation of the outer sheath, the coupling mechanism having a second condition in which the outer sheath is rotationally uncoupled from the steering catheter so that rotation of the steering catheter about the longitudinal axis does not result in a corresponding rotation of the outer sheath.

Another embodiment of a delivery system for delivering a prosthetic heart valve to a targeted anatomical site within a patient includes a catheter assembly including an outer sheath extending in a longitudinal direction between a proximal end and a distal end; a connecting arm connected to the outer sheath at the proximal end, the connecting arm extending away from the outer sheath in a direction transverse to the longitudinal direction; a valve cover at the distal end of the outer sheath, the valve cover having a proximal end, a distal end, and a size and a shape for housing the medical device in a collapsed condition; and a steering catheter coaxially arranged within the outer sheath, the steering catheter having a longitudinal axis and a flexible distal portion capable of deflecting in multiple directions relative to the longitudinal axis, wherein deflection of the distal portion of the steering catheter causes a corresponding deflection of a distal portion of the outer sheath; a handle connected to the steering catheter such that rotation of the handle causes a corresponding rotation of the steering catheter about the longitudinal axis; and a coupling mechanism including a rigid rod having a proximal end fixedly connected to the handle and extending in the longitudinal direction to a distal end; a rider slidably mounted on the rod; and a clip releasably connecting the rider to the connecting arm, wherein the coupling mechanism has a first condition in which the rider is connected to the connecting arm so that rotation of the steering catheter about the longitudinal axis results in a corresponding rotation of the outer sheath, and the coupling mechanism has a second condition in which the rider is released from the connecting arm so that rotation of the steering catheter about the longitudinal axis does not result in a corresponding rotation of the outer sheath.

BRIEF DESCRIPTION OF THE DRAWINGS

A more complete appreciation of the subject matter of the present disclosure and the various advantages thereof can be realized by reference to the following detailed description in which reference is made to the accompanying drawings in which.

DETAILED DESCRIPTION

As used herein, the term “inflow end,” when used in connection with a prosthetic heart valve, refers to the end of the heart valve through which blood enters when the heart valve is functioning as intended, whereas the term “outflow end,” when used in connection with a prosthetic heart valve, refers to the end of the heart valve through which blood exits when the heart valve is functioning as intended. For a prosthetic mitral valve, the inflow end is closest to the left atrium when the heart valve is implanted in a patient, and the outflow end is closest to the left ventricle when the heart valve is implanted in a patient. Further, when used herein in connection with a delivery device, the terms “proximal” and “distal” are to be taken as relative to a user operating the device in an intended manner. “Proximal” is to be understood as relatively close to the user and “distal” is to be understood as relatively farther away from the user. Also as used herein, the terms "substantially," "generally," and "about" are intended to mean that slight deviations from absolute are included within the scope of the term so modified.

In the description which follows, a delivery system and the components thereof are described in connection with the delivery, positioning and deployment of a prosthetic mitral valve at the native mitral valve annulus. However, it is to be understood that the delivery system and components described also may be used to deliver, position and deploy prosthetic replacements for other cardiac valves, such as the aortic valve, the pulmonary valve and the tricuspid valve, as well as other medical devices. Exemplary prosthetic heart valves that can be used with the delivery system described herein include the expandable prosthetic heart valves described in U.S. Patent Publication No. 2016/0158000; in U.S. Pat. Nos. 8,870,948 and 10,470,881; and in PCT Publication No. WO 2016/183526, the disclosures of all of which are hereby incorporated by reference herein.

Figure 1A:
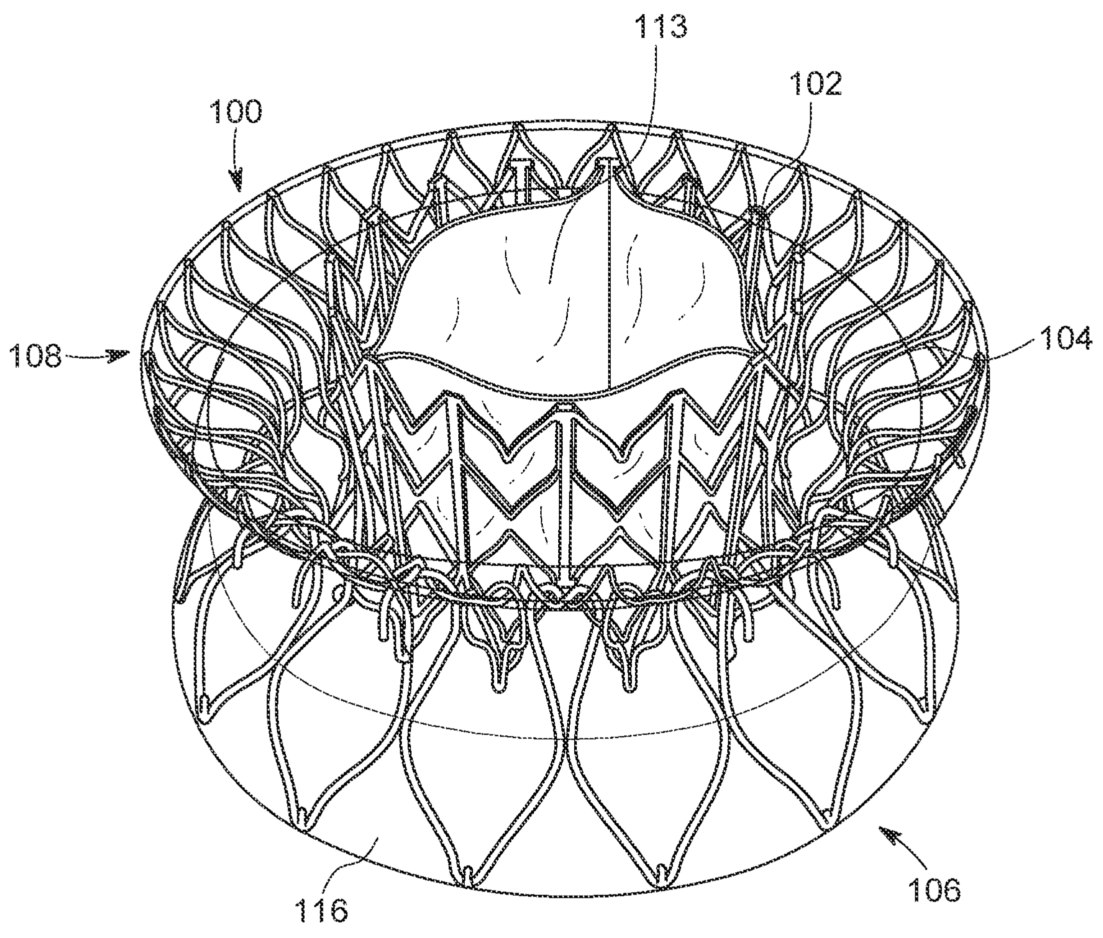
FIG. 1A is an illustrative prosthetic heart valve according to the prior art for use in conjunction with the delivery system of the present invention.
Figure 1B:
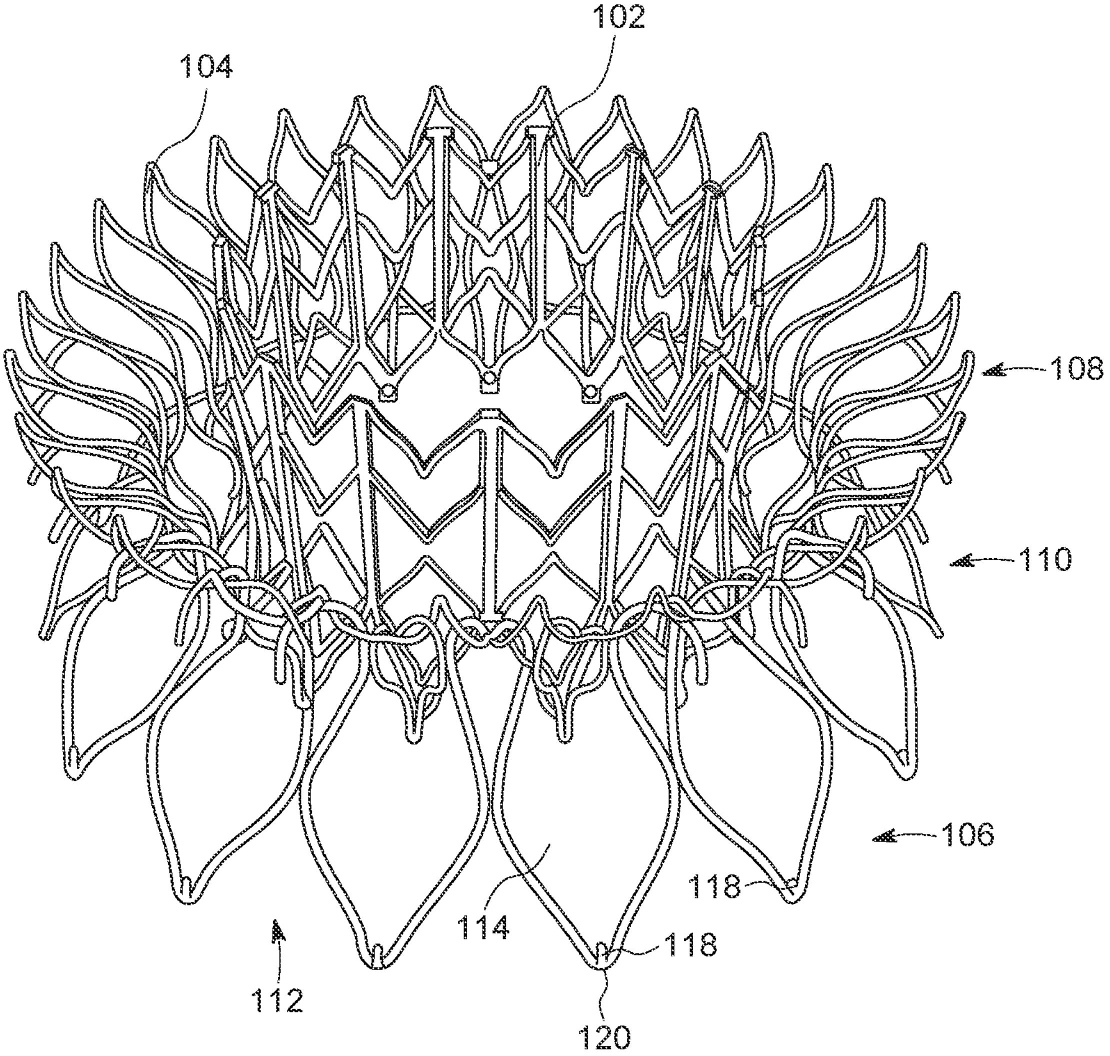
FIG. 1B is a perspective view of the frame structure of the prosthetic heart valve of FIG. 1A.

FIG. 1A is a perspective view of an exemplary prosthetic heart valve 100 that may be delivered, positioned and deployed by the delivery system disclosed herein. Prosthetic heart valve 100 may be a prosthetic mitral valve having an expandable and collapsible frame structure that includes an inner strut frame 102 surrounded by an outer anchor assembly 104, as shown in FIG. 1B. Anchor assembly 104, shown in an expanded state, includes an atrial anchor 106 configured to be positioned on the atrial side of the native mitral valve annulus, a ventricular anchor 108 configured to be positioned on the ventricular side of the native mitral valve annulus, and a central portion 110 positioned axially between the atrial anchor and the ventricular anchor. Anchor assembly 104 may have an hourglass shape in the expanded state in that each of atrial anchor 106 and ventricular anchor 108 flares radially outward of central portion 110, such that the central portion defines a waist between the atrial anchor and the ventricular anchor. Strut frame 102 may be positioned radially inward of anchor assembly 104 and may be formed of a plurality of interconnected struts. The radially inner surface of strut frame 102 defines the perimeter of a central opening 112, which enables blood to flow through prosthetic mitral valve 100.

Prosthetic mitral valve 100 includes one or more leaflets 113 that may be secured to strut frame 102 and disposed at least partially in central opening 112. Leaflets 113 are configured to coopt with one another to control blood flow through the prosthetic mitral valve, allowing blood to flow from atrial anchor 106 at the inflow end of the heart valve toward ventricular anchor 108 at the outflow end of the heart valve (the antegrade direction), but substantially blocking blood from flowing in the opposite (retrograde) direction. In some embodiments, one or more skirts or cuffs 116 may partially or fully cover inner and/or outer surfaces of anchor assembly 104 and/or strut frame 102. Such skirts or cuffs may be formed from fabric and/or tissue materials, for example, as may leaflets 113.

Both the atrial anchor 106 and the ventricular anchor 108 of anchor assembly 104 include a plurality of petals 114 that are joined to one another around the circumference of the anchor assembly. When prosthetic mitral valve 100 is in a fully expanded state, the petals 114 on both atrial anchor 106 and ventricular anchor 108 are fully extended radially outward, as shown in FIG. 1B. Prosthetic mitral valve 100 is naturally in an expanded state when no force is applied to petals 114. The petals 114 of anchor assembly 104 may be configured to collapse and/or to reduce the outer diameter of the frame structure when the prosthetic heart valve is loaded into a delivery device. When prosthetic mitral valve 100 is in a collapsed state, the petals 114 on both atrial anchor 106 and ventricular anchor 108 are at least partially collapsed radially inward. Prosthetic mitral valve 100 may be placed in the collapsed state by applying pressure to petals 114 in a radially inward direction.

The petals 114 on atrial anchor 106 or ventricular anchor 108 may include a pin 118 or other attachment member to which tether loops may be connected, as will be described below. Pins 118 may be attached to or formed on some or all of the petals 114 on atrial anchor 106 and/or ventricular anchor 108 and are sized and shaped so that the tether loops remain attached when under tension but are released from the frame structure after the deployment of prosthetic mitral valve 100 within the patient. Pins 118 may be provided, for example, at the apex 120 of each petal 114 on atrial anchor 106. However, this need not be the case and pins 118 may be provided on less than all of the petals 114 of atrial anchor 106, on some or all of the petals of ventricular anchor 108, or at other locations on anchor assembly 104.

Figure 2:
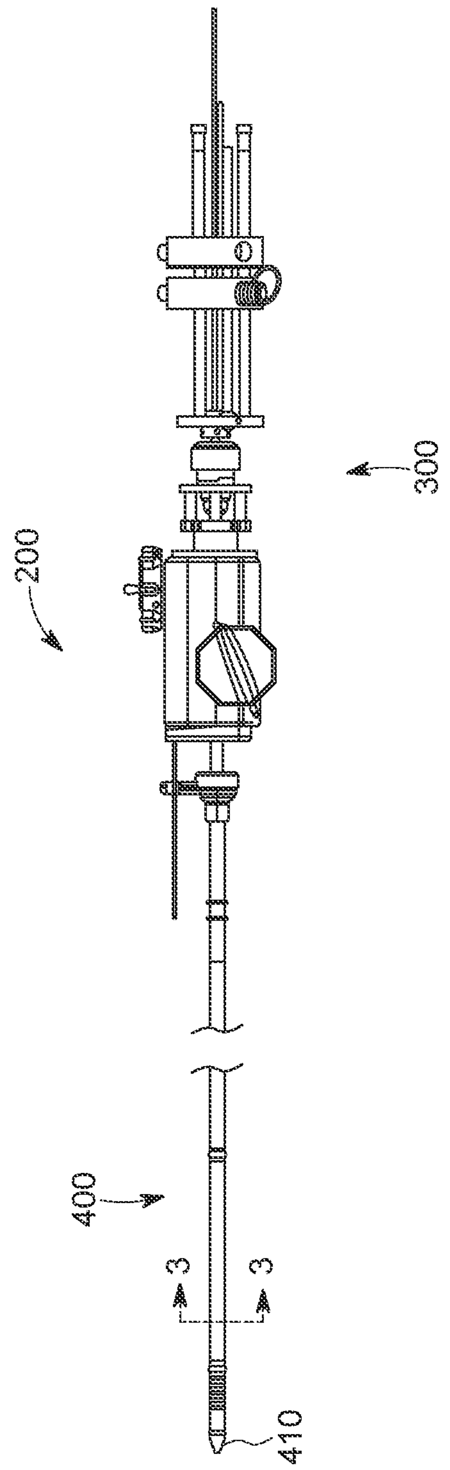
FIG. 2 is a side view of a delivery system configured for delivering, positioning and deploying a prosthetic heart valve, including a handle assembly and a catheter assembly.
Figure 3A:
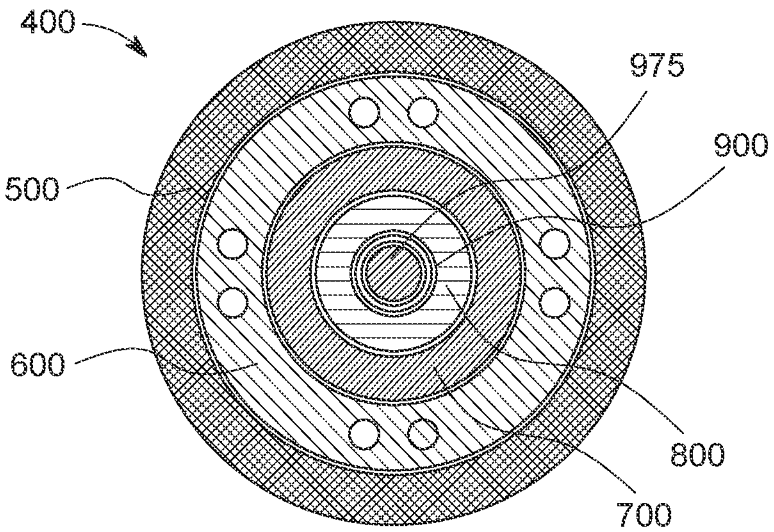
FIG. 3A is a transverse cross-sectional view of the catheter assembly of FIG. 2, showing the various components thereof.
Figure 3B:
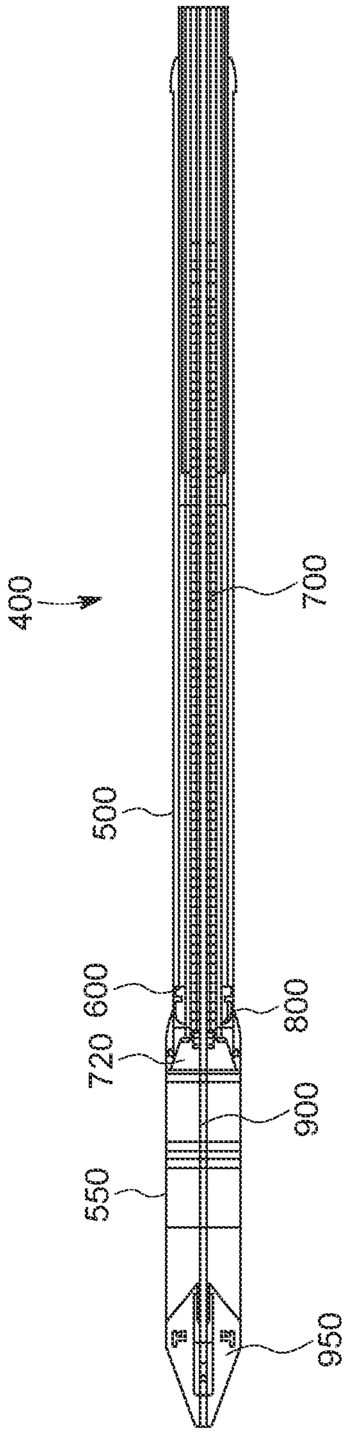
FIG. 3B is a longitudinal cross-section of the catheter assembly of FIG. 2, showing the nested arrangement of the various components thereof.

FIG. 2 illustrates an exemplary embodiment of a delivery system 200 for delivering and deploying a prosthetic heart valve at a target location within the patient's heart. Delivery system 200 generally includes a handle assembly 300 and a catheter assembly 400. Catheter assembly 400 extends from a proximal end coupled to handle assembly 300 to an atraumatic tip 410 at a distal end and includes a plurality of catheter and/or hypotube components that are longitudinally slidable relative to one another and that provide different functionality during operation of delivery system 200 to enable effective delivery and deployment of a prosthetic heart valve, such as prosthetic mitral valve 100. As shown in FIG. 3A, which is a cross-sectional view of catheter assembly 400 taken along line 3-3 of FIG. 2, these components include an outer sheath 500, a steering catheter 600, an extension catheter 700, a suture catheter 800, and a nosecone catheter 900, all arranged in a concentric nested relationship. The arrangement of these components, as well as valve cover 550 and nosecone 950, is shown in the longitudinal cross-section of catheter assembly 400 shown in FIG. 3B. As illustrated in the figures, nosecone catheter 900 has a lumen sized to receive a guidewire 975 therein. Each of these components is described in detail below.

Figure 4:
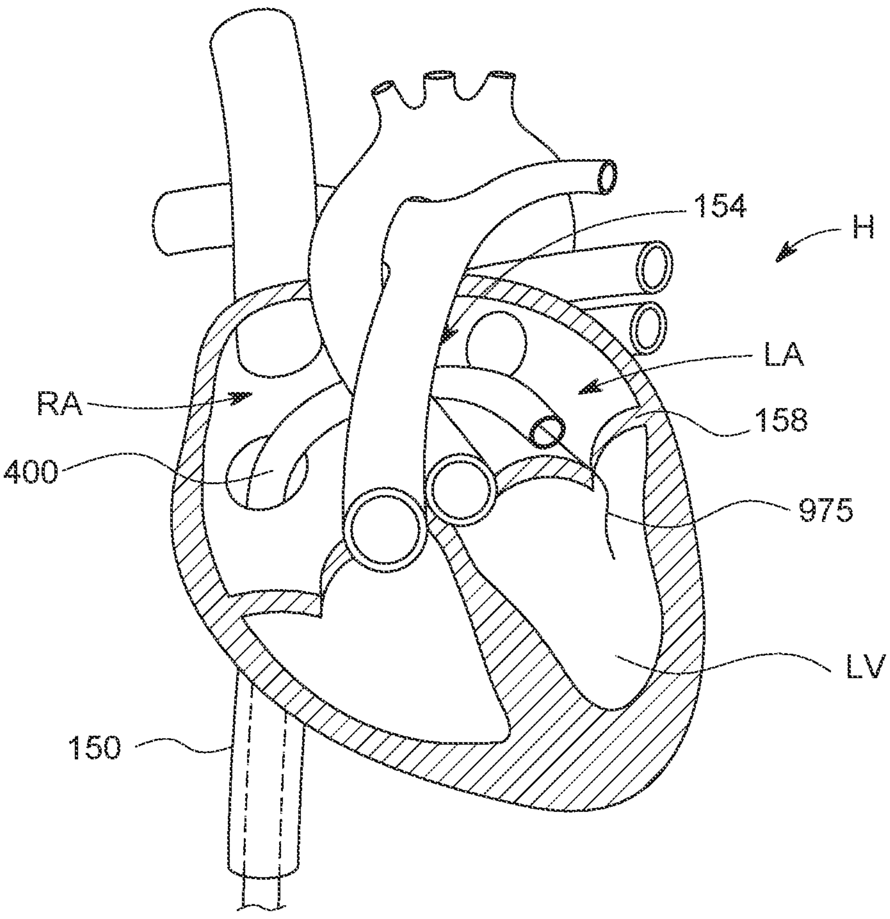
FIG. 4 is a schematic cutaway view of the heart, showing an exemplary approach for delivering the prosthetic heart valve to the mitral valve annulus.

FIG. 4 is a schematic representation of a patient's heart H and a delivery route that may be followed by catheter assembly 400 to reach the native mitral valve annulus 158. Using a transfemoral approach, catheter assembly 400 may be inserted into the patient's femoral vein and advanced through the inferior vena cava 150 to the right atrium RA. In a subsequent transseptal procedure, catheter assembly 400 is advanced through a puncture in intra-atrial septum 154 into the left atrium LA.

In other implementations, such as for procedures associated with a tricuspid valve, catheter assembly 400 may be advanced through the inferior vena cava 150 and into the right atrium RA, where it may then be positioned and used to perform the procedure related to the tricuspid valve. While many of the examples described herein relate to delivery to the native mitral valve annulus, one or more embodiments may be utilized in other cardiac procedures, including those involving the tricuspid valve or other cardiac valves.

Although one preferred method for accessing a targeted cardiac valve annulus is a transfemoral approach, it will be understood that the embodiments described herein may also be utilized where alternative approaches are used. For example, embodiments described herein may be utilized in a transjugular approach, transapical approach, transradial approach or other suitable approaches to the targeted anatomy. For procedures related to the mitral valve or tricuspid valve, the delivery of the prosthetic heart valve or other medical device is preferably carried out from an atrial aspect (i.e., with the distal end of catheter assembly 400 positioned within the atrium superior to the targeted valve). The illustrated embodiments are shown from such an atrial aspect. However, it will be understood that the delivery of the medical devices described herein may also be carried out from a ventricular aspect.

Additional details regarding delivery systems and devices that may be utilized in conjunction with the components and features described herein are described in U.S. Patent Publication Nos. 2018/0028177A1, 2018/0092744A1, and 2020/0155804, the disclosures of which are hereby incorporated by reference herein.

Figure 5:
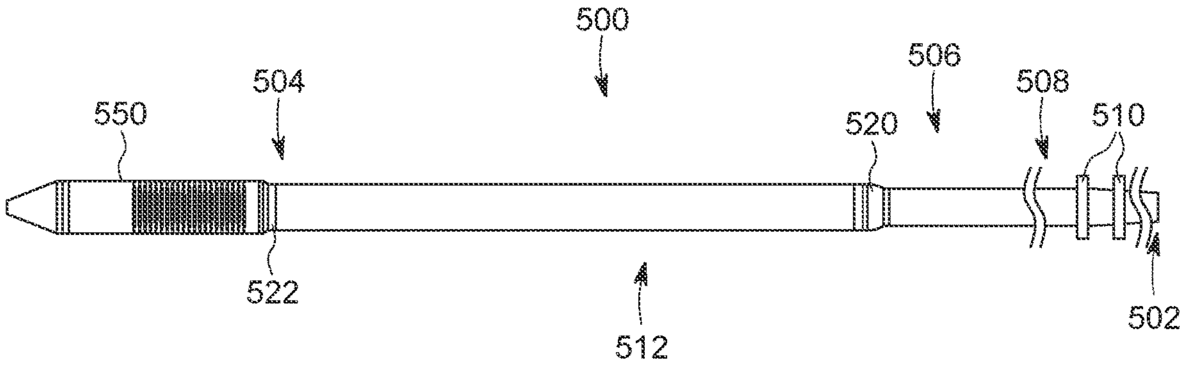
FIG. 5 is a side view of an outer sheath of the catheter assembly, showing the nosecone in a closed position at the distal end thereof.
Figure 6:
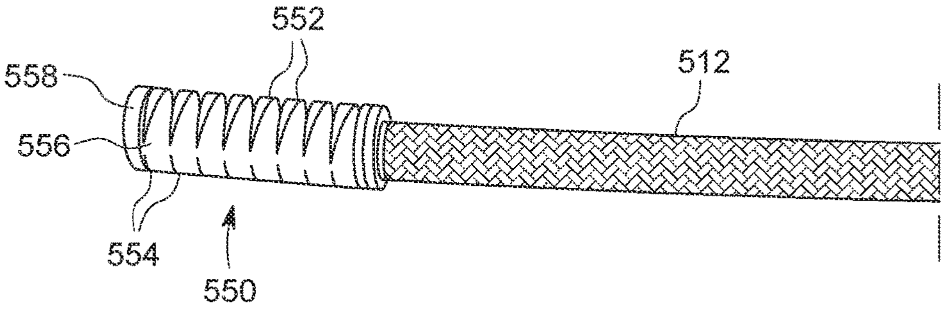
FIG. 6 is an enlarged view of the distal end of the outer sheath and valve cover shown in FIG. 5.
Figure 7:
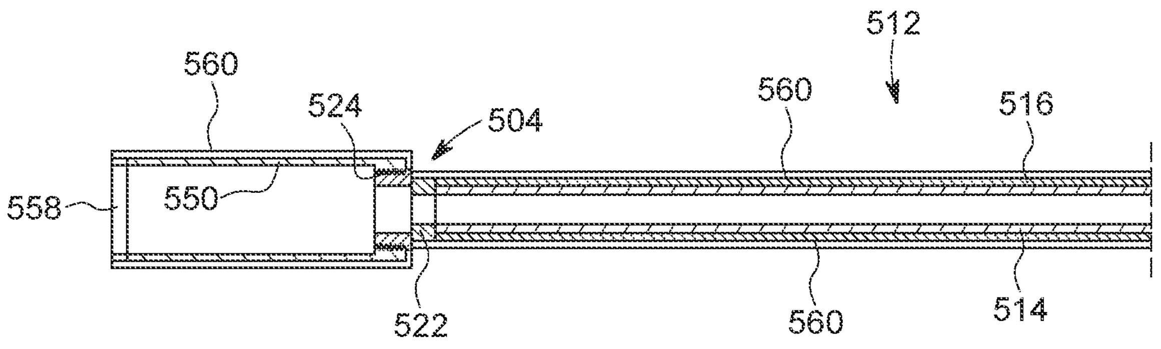
FIG. 7 is a longitudinal cross-section of the distal end of the outer sheath and the valve cover shown in FIG. 6.

As noted, the outer component of catheter assembly 400 is outer sheath 500, shown in FIGS. 5-7. Outer sheath 500 extends from a proximal end 502 to a distal end 504. A proximal portion 506 of outer sheath 500 may be formed from a stainless-steel hypotube having a plurality of slits (not shown) laser cut in an interrupted spiral pattern along a majority of its length. The slits begin at a spaced distance from the proximal end 502 of outer sheath 500, leaving an uncut portion 508 that enables the proximal end of the outer sheath to be fixedly connected, such as by adhesive, to a hemostasis valve 530 (see, for example, FIG. 17) with a leakproof seal. A pair of fixed rings 510 may be spaced apart from one another around the outside of uncut portion 508. Rings 510 enable outer sheath 500 to be held in place as other components of catheter assembly 400 are advanced or retracted, and also enable the outer sheath itself to be retracted for deploying prosthetic mitral valve 100, as will be discussed further below. Although outer sheath 500 is described as formed from a stainless-steel hypotube, that need not be the case. Outer sheath 500 may alternatively be formed from other metals or metal alloys, including titanium or tantalum, from biologically stable polymers, from biologically stable composites, from a braided polymer shaft (as long as the shaft can transmit the axial forces needed to unsheathe a valve), and the like.

Figure 8:
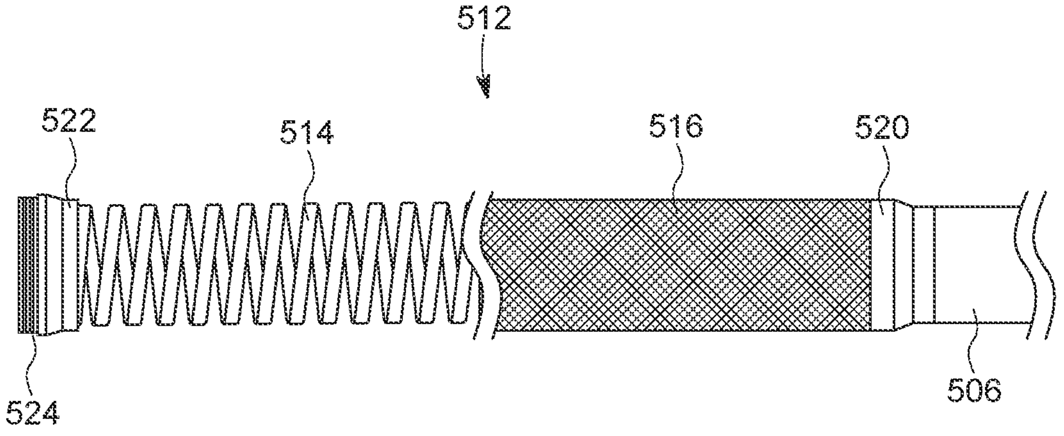
FIG. 8 is an enlarged cutaway view of a highly flexible portion of the outer sheath.

FIGS. 6 and 7 illustrate a distal portion of outer sheath 500 and a connected valve cover 550. The distal portion of outer sheath 500 includes a highly flexible portion 512 extending from proximal portion 506 to the distal end 504 of the outer sheath and having a sufficient length to surround and extend along that portion of catheter assembly 400 that is designed to bend and reorient to navigate through a patient's vasculature and heart to reach mitral valve annulus 158 for deployment of the prosthetic heart valve. In some embodiments, flexible portion 512 may have an inner coiled layer 514 formed from a coiled wire and an outer braided sleeve 516 covering the coiled layer (sometimes collectively referred to as "coil/braid portion 514/516"), as shown in FIG. 8. Coiled layer 514 is formed so that there are spaces between adjacent turns of the coil. In some embodiments, the spaces between adjacent turns of the coil are greater than the cross-section of the wire forming the coil. In such embodiments, longitudinally compressing the coil to eliminate the spaces between adjacent turns can reduce the overall length of coiled layer 514 by about 50% to about 70% or more of its original length. Braided sleeve 516 may be fixedly connected at its proximal and distal ends to coiled layer 514 by soldering through the filaments of the braid. The resultant coil/braid portion 514/516 exhibits a high degree of flexibility.

A stainless-steel ring 520 may be laser welded to the proximal end of coiled layer 514. As ring 520 is not covered by braided sleeve 516, it enables the proximal end of flexible portion 512 to be laser welded to the proximal portion 506 of outer sheath 500. Another stainless-steel ring 522 may be laser welded to the distal end of coiled layer 514, followed by another stainless-steel ring 524 that has a slightly larger diameter and that is externally threaded. The external threads provide for a threaded connection of valve cover 550 to coil/braid portion 514/516, and the slightly larger diameter of ring 524 enables the connection to be made without any exposed edges. A threaded connection enables valve cover 550 to be removably connected to outer sheath 500. Additionally, a threaded connection facilitates the joining of dissimilar metals, such as titanium valve cover 550 to a stainless-steel outer sheath 500. However, when possible, the valve cover alternatively may be laser welded to the outer sheath. In a further variant, braided sleeve 516 may be connected to coiled layer 514 by adding the small rings 520 and 522 over the proximal and distal ends, respectively, of the coil/braid portion 514/516 and laser welding all three components together simultaneously.

As outer sheath 500 is retracted to deploy the prosthetic heart valve, internal friction between collapsed prosthetic mitral valve 100 and the valve cover 550 in which it is housed will inhibit the retraction of coiled layer 514, causing the individual coils to slightly separate farther from one another and braided sleeve 516 to lengthen. As braided sleeve 516 lengthens, its diameter will collapse around coiled layer 514, much like a Chinese finger trap, preventing further lengthening of coil layer 514 while still retaining the flexibility of flexible portion 512. Further, the collapse of braided sleeve 516 around coiled layer 514 keeps flexible portion 512 round when it is bent, preventing it from assuming an oval shape that could make it difficult to retract outer sheath 500 to deploy the prosthetic heart valve.

Valve cover 550 defines a compartment for housing prosthetic mitral valve 100 in a compressed, pre-deployed state during intravascular delivery of the prosthetic valve to the targeted cardiac site. Valve cover 550 may be in the form of a generally cylindrical very thin-walled tube of a hard, lightweight metal, such as titanium, having an inner diameter and length sized to receive the prosthetic mitral valve in a collapsed condition. In some embodiments, valve cover 550 may have a wall thickness of between about 0.10 mm (or thinner) and about 0.50 mm, or between about 0.30 mm and about 0.40 mm. A series of internal threads (not shown) may be cut at the proximal end of valve cover 550 for engagement with the external threads of ring 524 at the distal end of outer sheath 500.

Titanium is sufficiently inert that it will not interact with or contaminate, or is less likely to interact with or contaminate, the nitinol forming the frame 102 of prosthetic mitral valve 100 as the valve is retracted into and held within valve cover 550. A series of V-shaped cuts 552 may be laser cut along one side of valve cover 550, and a series of slits 554 may be laser cut along the diametrically opposed side of the valve cover, leaving a pair of continuous longitudinal spines 556 along opposite sides of the valve cover. The series of cuts 552 and slits 554 enable valve cover 550 to bend in a single plane. As valve cover 550 bends, cuts 552 will collapse, while slits 554 will open. Preferably, cuts 552 and slits 554 are sufficient to enable valve cover 550 to bend about 75° or more; preferably, about 90° or more, or about 150° or more, so that the valve cover can be pulled over the distal bend of the steering catheter as it is retracted during deployment of prosthetic mitral valve 100. Cuts 552 and slits

554 are not formed along a distal section of valve cover 550 so as to not interfere with the protruding tines of the prosthetic mitral valve 100 as the prosthetic valve is retracted into the valve cover. Although the foregoing describes the use of titanium to form valve cover 550, other sufficiently strong and inert metals and metal alloys may also be used to form the valve cover.

The spines 556 formed along opposite sides of valve cover 550 between cuts 552 and slits 554 provide the valve cover with sufficient tensile strength to withstand the retraction of outer sheath 500 during deployment of a prosthetic heart valve. The distal end of valve cover 550 may have a number of external threads (not shown) to attach a loading funnel to the valve cover. After prosthetic mitral valve 100 has been loaded into valve cover 550 and the funnel has been removed, a tantalum ring 558 may be threaded onto the distal end of the valve cover to cover the threads and ensure a smooth surface. When formed from a very radiopaque material such as tantalum, platinum, iridium, gold or other materials with a high atomic number, ring 558 helps the user locate the end of valve cover 550 under x-ray imaging to assure the proper location and orientation of the valve cover for deployment of the prosthetic valve. Rather than incorporating threads at the proximal end of valve cover 550 for a removable connection to outer sheath 500 and at the distal end of the valve cover for the removable connection of ring 558, other removable connecting mechanisms may be used, including snap connections, bayonet connections and the like.

The entire length of outer sheath 500 and valve cover 550 may be covered by a flexible, elastic, fluid-impermeable jacket 560 to seal the slits in the proximal portion 506 and the coil/braid portion 514/516 in the flexible portion 512 of the outer sheath and the cuts 552 and slits 554 in the valve cover. Alternatively, jacket 560 may extend only from valve cover 550 to a location just proximal of coil/braid portion 514/516, and another fluid-impermeable jacket may be applied over the slits in the proximal portion 506 of outer sheath 500. In yet another arrangement, jacket 560 may be interposed between the coiled layer 514 and braided sleeve 516 of outer sheath 500, with other fluid-impermeable layers over valve cover 550 and the slits in the proximal portion 506 of the outer sheath. Any of these arrangements may be employed, as long as a liquid-tight structure results. The purpose of the fluid-impermeable layer or layers is to enable the entirety of catheter assembly 400 to be flushed with a saline solution to remove all air. Jacket 560 may be formed from a tube of Texin® synthetic resin available from Covestro LLC, or from another elastic material. After the application of jacket 560, the proximal and distal ends of the jacket may be bonded to the underlying structure using thermal adhesives, UV-bonded adhesives, other types of adhesives, thermal boding, heat shrinking or other techniques.

Figure 9:
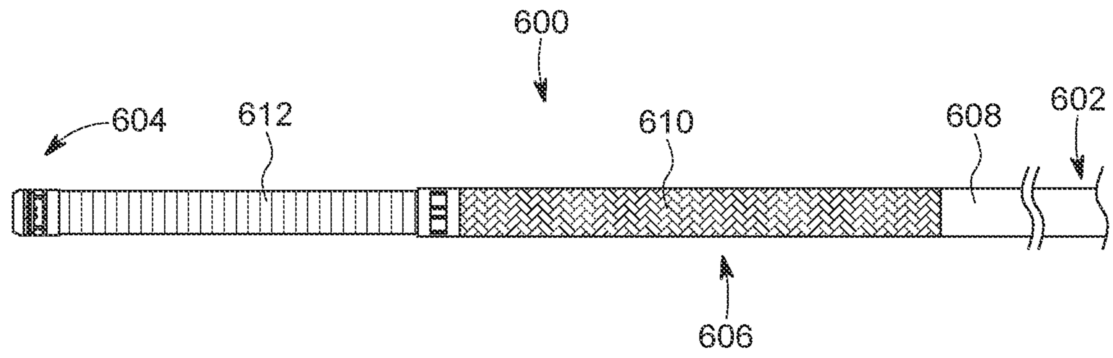
FIG. 9 is a side view of a steering catheter of the catheter assembly, showing various sections thereof.

Steering catheter 600 may be nested within outer sheath 500 and may extend from a proximal end 602 connected to steering catheter handle 132 to a distal end 604. Steering catheter 600 is configured to be selectively curved to facilitate navigation through the patient's vasculature and portions of the heart. Referring to FIG. 9, steering catheter 600 may be formed from a stainless-steel hypotube 606 having a proximal section 608, an intermediate section 610 and a distal section 612. The proximal section 608 of hypotube 606 may be uncut to provide steering catheter 600 with a desired amount of stiffness, torquability and pushability, as well as the ability to form a leakproof connection with steering catheter handle 132. Intermediate section 610 and distal section 612, on the other hand, may be laser cut in a way that enables each section to have sufficient flexibility to achieve a desired bending radius. Intermediate section 610 may be laser cut in an interrupted spiral pattern along its length, much like the proximal portion 506 of outer sheath 500, and may include an outer metal braided layer. Distal section 612 may include a plurality of V-shaped or island cuts and slits, similar to those in valve cover 550, formed along opposite sides of hypotube 606, with each successive pair of cuts and slits being offset in the circumferential direction from an adjacent pair of cuts and slits by 90°. This arrangement of cuts and slits enables distal section 612 to be deflected within one, two or three planes orthogonal to one another. Although steering catheter 600 has been described above with interrupted spiral cuts in intermediate section 610 and V-shaped cuts and slits in distal section 612, other cutting patterns and shapes are possible. For example, a series of narrow slits may be formed along one side of steering catheter 600, the slits enabling longitudinal forces to be transmitted along the catheter and allowing expansion of the catheter when it is deflected in a direction opposite the slits. A series of wider island cuts may be formed along the side of steering catheter 600 opposite the slits, the island cuts allowing compression of the catheter when it is deflected in the direction of the island cuts. The island cuts may be formed so that they progressively change in size in the length direction of steering catheter 600. For example, the island cuts may progressively get smaller in the distal direction along the length of steering catheter 600, providing a gradient bend that gradually increases in deflection at successively more proximal sections.

Figure 10A:
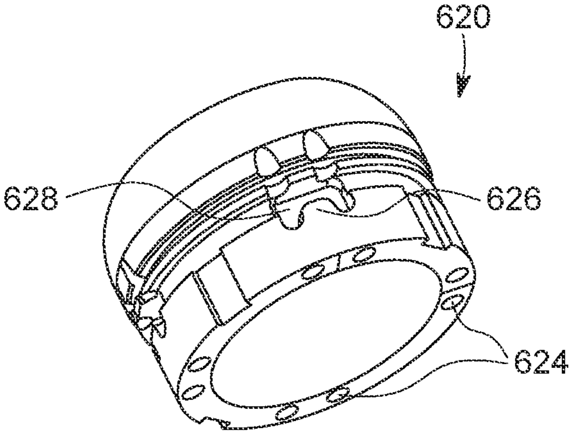
FIG. 10A is a perspective view of a tip ring that may be used at the distal end of the steering catheter.
Figure 10B:
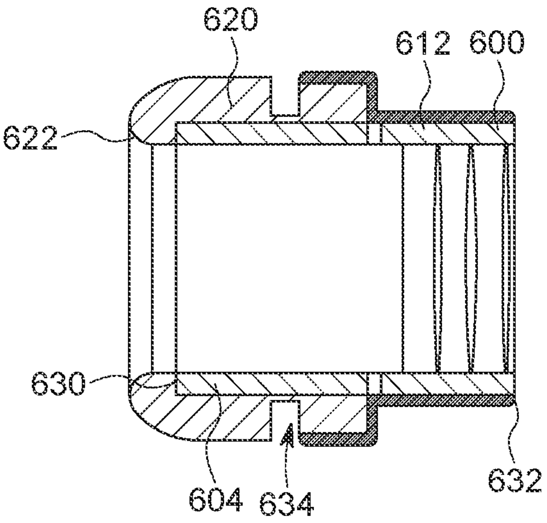
FIG. 10B is a longitudinal cross-section of the tip ring of FIG. 10A connected to the distal end of the steering catheter.

A steering or tip ring 620, shown in FIGS. 10A and 10B, may be secured to the distal end 604 of steering catheter 600. As best shown in the cross-sectional view of FIG. 10B, tip ring 620 may have an angled or rounded distal edge 622 that enables steering catheter 600 to more effectively move and slide within outer sheath 500 without binding, and that prevents binding against components intended to translate within the steering catheter, such as extension catheter 700.

To selectively control the curvature of the distal section 612 of steering catheter 600, the steering catheter may be provided with a plurality of tension cables (not shown). The tension cables may travel from steering catheter handle 132 through a plurality of polymer tubes to the tip ring 620 at the distal end 604 of steering catheter 600. In one embodiment, steering catheter 600 may include four polytetrafluoroethylene (PTFE) tubes equally spaced at 90° intervals around the circumference of hypotube 606. In another embodiment, steering catheter 600 may include four pairs of PTFE tubes (a total of eight tubes), with the pairs of tubes equally spaced at 90° intervals around the circumference of hypotube 606. Any number of these tubes may be provided depending on the various directions of deflection that may be desired. Tip ring 620 may include a plurality of apertures 624 spaced in pairs around its circumference, with a seat 626 and a cutout 628 longitudinally aligned distally of each aperture pair. Each tension cable may travel distally through one of the tubes, through one of a pair of apertures 624 in tip ring 620, through a cutout 628 and around a seat 626, and then proximally though the other aperture in the pair. At that point, the tension cable may travel proximally through the same tube (when there are four tubes) or through another tube (when there are eight tubes) back to the proximal end 602 of steering catheter 600 where the cable ends are attached to and controlled by steering catheter handle 132, as will be explained below. One or more tension cables may additionally or alternatively be coupled at its distal end to the intermediate section 610 of steering catheter 600 to provide the ability to selectively control the curvature of the intermediate section. A polymer layer 632 formed, for example, from Pebax, may be provided as an outer layer surrounding a portion of tip ring 620 and steering catheter 600, including the tubes guiding the tension cables, to produce a liquid-tight structure and impart substantial lubricity to the steering catheter.

One of the functions of delivery system 200 is to position the distal tip of catheter assembly 400 so that prosthetic mitral valve 100 can be deployed in the proper location. This may be accomplished by bending steering catheter 600 in two separate planes via a transseptal approach.

Figure 11:
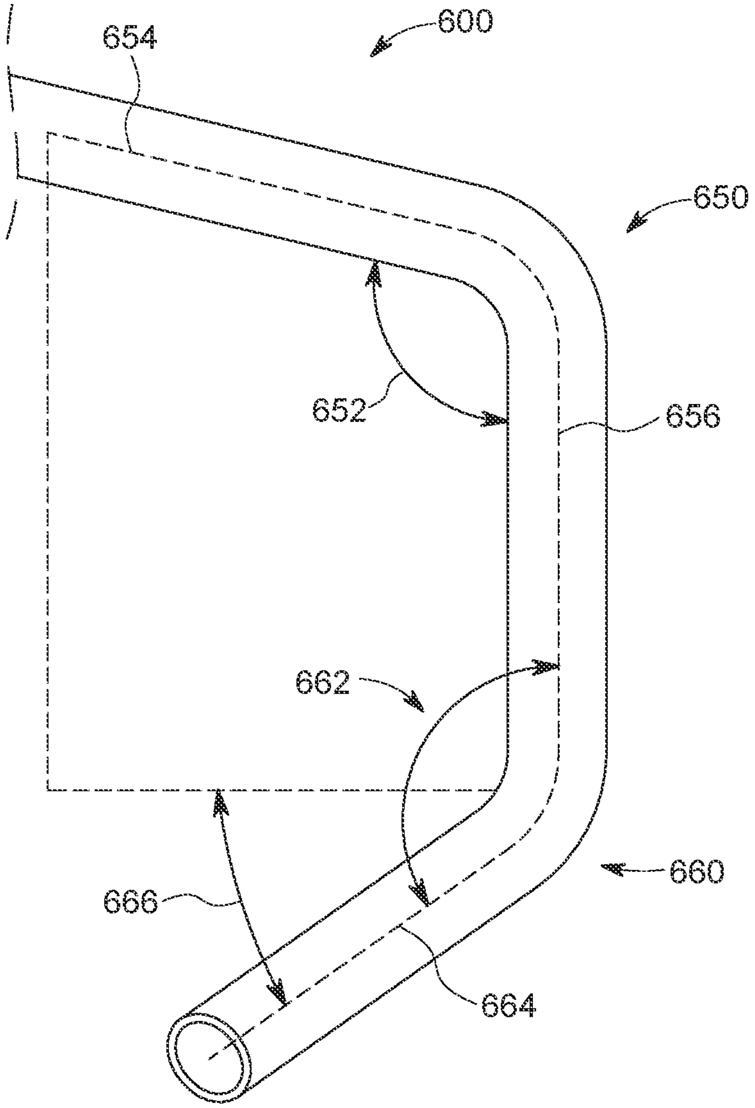
FIG. 11 is an enlarged partial view of the distal section of the steering catheter of FIG. 9 forming a compound curve shape to enable proper positioning of the catheter assembly relative to the mitral valve annulus.

FIG. 11 illustrates an example of a series of complex bends that the distal section 612 of steering catheter 600 may make during the delivery, recapture or repositioning of a prosthetic mitral valve. While accessing the mitral valve annulus, the distal section 612 of steering catheter 600 may be steered in at least two planes of motion that may be substantially perpendicular to one another. In the illustrated example, steering catheter 600 has a first bend 650 with a first bend angle 652 measured between the longitudinal axis 654 of a first portion of the steering catheter and the longitudinal axis 656 of a second portion of the steering catheter. In some embodiments, the first bend angle 652 may be between about 40° and about 150°, more often between about 90° and about 120°, or about 105°. Steering catheter 600 may also have a second bend 660 with a second bend angle 662 between longitudinal axis 656 and the longitudinal axis 664 of a third portion of the steering catheter. In one embodiment, the second bend angle 662 may be between about 45° and about 135°, or about 60°. The second bend 660 may also have a rotational angle 666 relative to the plane in which the first longitudinal axis 654 and the second longitudinal axis 656 lie. In other words, the rotational angle 666 reflects the amount of rotation of the third longitudinal axis 664 relative to the direction of the first bend 650. In some embodiments, the rotational angle 666 may be between about 45° and about 135°, or about 60°. In some embodiments, steering catheter 600 may achieve bend angles of up to 180°.

The distal-most section of steering catheter 600 preferably has a relatively straight section. This may be manifest as an uncut section at the distal end 604 of steering catheter 600. The uncut, relatively straight section allows the components advancing past the distal end 604 of steering catheter 600 to continue along a straight path. For example, by pointing the distal end 604 of steering catheter 600 directly at the mitral valve annulus, the components advancing distally beyond the steering catheter (such as, for example, extension catheter 700) will continue on a straight trajectory toward/through the annulus. Moving proximally from the straight, uncut section, the bend in steering catheter 600 may form gradually before increasing to form the full bend. Other methods of achieving a straight section at the end of steering catheter 600 are also possible. In one example, can 720 described below can be attached directly to the tip ring 620 of the steering catheter, and the can may be provided with a straight section. In another example, the tip ring 620 of the steering catheter itself may be provided with a straight section.

To provide effective steering and positioning at the mitral annulus, the distal section 612 of steering catheter 600 may be cut with a pattern that enables a bending radius of about 15 mm or less, or between about 5 mm and about 15 mm. The intermediate section 610 of steering catheter 600 may be cut to enable a bending radius of between about 30 cm and about 45 cm. The proximal section 608 of steering catheter 600 may remain uncut to ensure that the steering catheter has sufficient stiffness, torquability and pushability to effectively operate, and to enable a leakproof connection between the steering catheter and steering catheter handle 132.

Figure 12A:
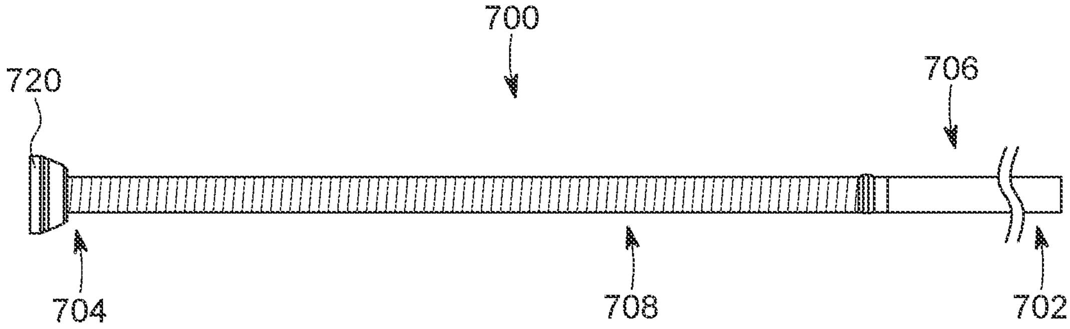
FIG. 12A is a side view of an extension catheter of the catheter assembly with a distal can structure at its distal end.
Figure 12B:
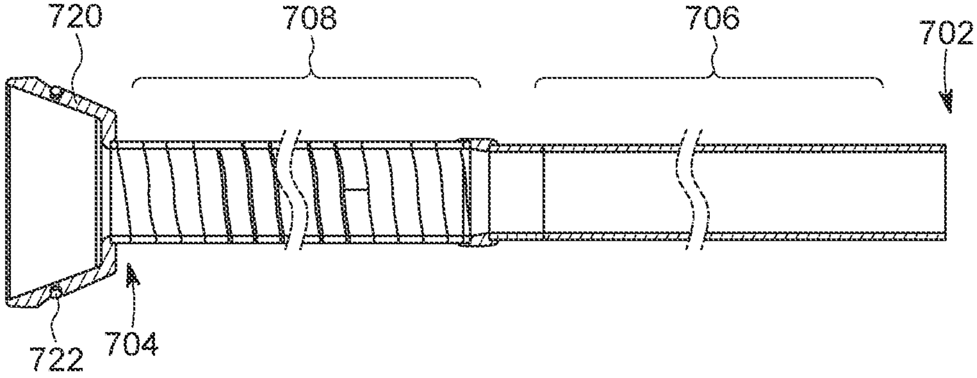
FIG. 12B is an enlarged partial cross-section of the distal section of the extension catheter and distal can structure of FIG. 12A.
Figure 12C:
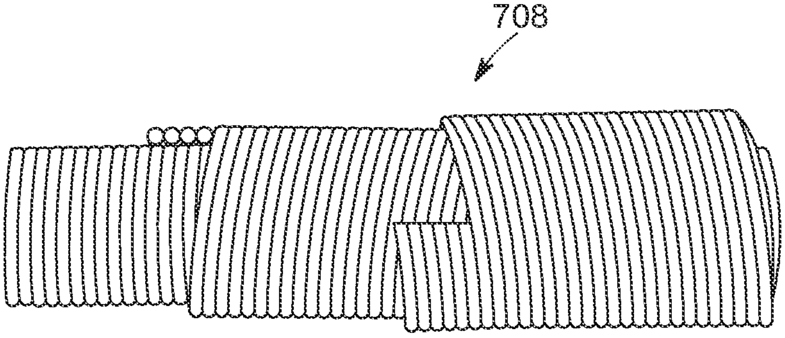
FIG. 12C is an enlarged highly schematic view illustrating the tri-coil structure in the distal section of the extension catheter.

Nested within steering catheter 600 is an extension catheter 700, one embodiment of which is shown in FIGS. 12A-12C. Alternate embodiments of extension catheter 700 having a structure and features other than those described herein may also be used. Extension catheter 700 may have to withstand relatively high compression forces during the deployment of a prosthetic heart valve. For example, during the release of prosthetic mitral valve 100 by the retraction of outer sheath 500, the countervailing compression force on extension catheter 700 may be on the order of about 30 to 50 lbs. Extension catheter 700 must also have sufficient flexibility to allow for proper deflection and curvature to achieve a desired position in the mitral valve annulus. A coil structure, such as in a distal section of extension catheter 700, is beneficial because it has high flexibility and is also able to withstand high compression forces. In some embodiments, the coil may be a flat wire stacked coil (i.e., a coil in which adjacent turns contact one another with no gaps between them), which has been found to provide an effective balance between flexibility and compressive strength.

Referring to FIGS. 12A and 12B, extension catheter 700 extends from a proximal end 702 to a distal end 704, with a proximal section 706 adjacent the proximal end and a distal section 708 adjacent the distal end. The proximal section 706 of extension catheter 700 may be formed from a stainless-steel hypotube having a laser cut interrupted spiral pattern of slits (not shown) beginning at a spaced distance from proximal end 702. The distal section 708 of extension catheter 700 may be formed with a tri-coil structure. That is, distal section 708 may be formed with three layers of wire coils, with the inner and outer layers being wound in the same direction, and the middle layer being wound in a direction opposite that of the inner and outer layers. An illustration of the tri-coil structure is shown in FIG. 12C. In one example, the inner coil may consist of a single wire or filar wound into a coil; and the middle and outer layers may each consist of a bundle of six filars arranged side-by-side and wound into a coil. Each of the individual filars may have a rectangular cross-section. Layers with coils having different numbers of filars are also contemplated. The three coils are coextensive and are welded to one another at their ends, as well as welded to proximal section 706. The tri-coil structure provides distal section 708 with enough flexibility to enable extension catheter 700 to be advanced distally through catheter assembly 400 when the distal end of steering catheter 600 has been deflected into a tight curve to align prosthetic mitral valve 100 with mitral annulus 158. As a result, extension catheter 700 is better able to maintain the position of prosthetic mitral 100 valve relative to native mitral annulus 158 as catheter assembly 400 is manipulated to deploy the prosthetic valve.

Extension catheter 700 includes a can structure 720 that may be laser welded to distal end 704. Can 720 is configured to constrain and hold at least the atrial petals 114 of prosthetic mitral valve 100. Without such constraint, atrial petals 114 may bend outwardly under compression when valve cover 550 is retracted, locking the prosthetic mitral valve inside the valve cover and making it more difficult to unsheathe or re-sheathe it. Can 720 also provides an effective structural surface to act as a counterforce to maintain the prosthetic heart valve in a proper pre-deployed position when outer sheath 500 is retracted.

A suture catheter 800 may be positioned within extension catheter 700. Generally, suture catheter 800 must have a sufficiently flexible distal end that is able to accommodate the tight curves at the distal end of steering catheter 600. In addition, suture catheter 800 must withstand substantial tension during the loading of prosthetic mitral valve 100 into valve cover 550 and must maintain axial tension on the prosthetic mitral valve prior to deployment. By maintaining such axial tension, suture catheter 800 may aid in maintaining the atrial petals 114 of the prosthetic valve within can 720 and the position of the prosthetic valve within catheter assembly 400, as will be described further below.

Figure 13A:
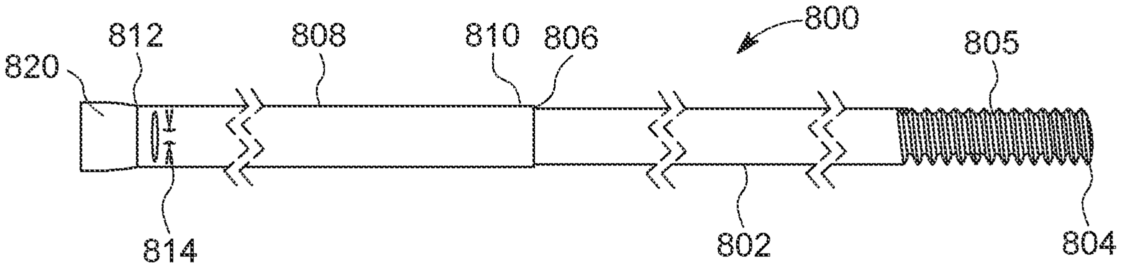
FIG. 13A is a side view of a suture catheter of the catheter assembly.
Figure 13B:
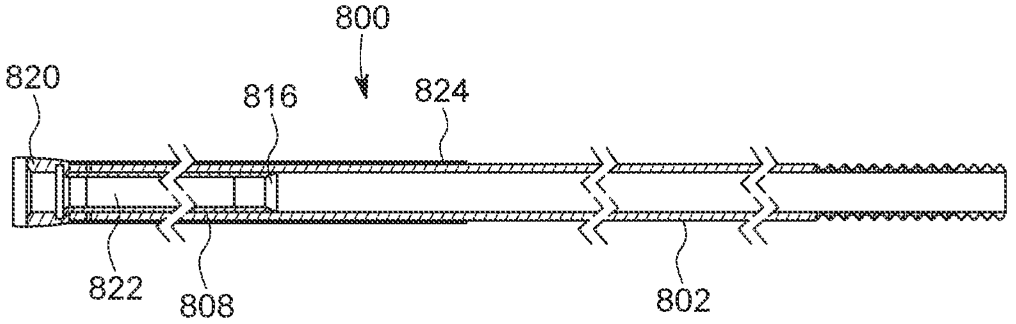
FIG. 13B is a longitudinal cross-section of the suture catheter of FIG. 13A.
Figure 13C:
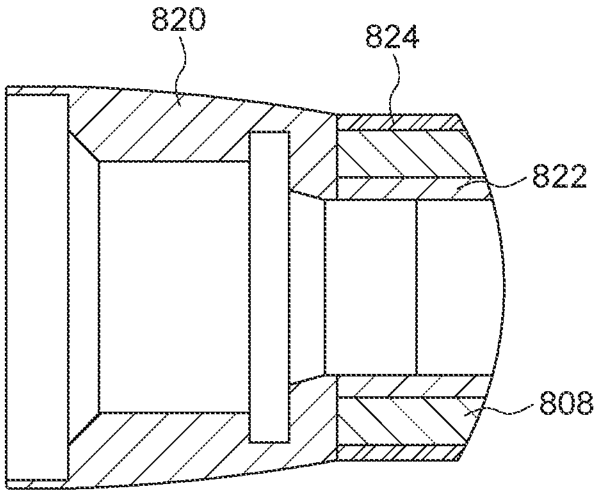
FIG. 13C is an enlarged longitudinal cross-section of the distal end of the suture catheter of FIG. 13A.

One embodiment of a suture catheter 800 is shown in FIGS. 13A-C, although embodiments of the suture catheter having alternative features and constructions are contemplated herein. Suture catheter 800 has a relatively long proximal portion 802 that may be formed from a stainless-steel hypotube having a proximal end 804 and a distal end 806. A portion of the hypotube adjacent proximal end 804 may include external threads 805 for attachment to the internal threads of a suture catheter control 870, as described below, although other mechanisms for attaching the suture catheter to the suture catheter control may also be used, including a snap fit connector, retaining clip, bayonet connector, and the like. The proximal portion 802 of suture catheter 800 may include an interrupted spiral pattern of slits cut along its length, the slits terminating at a spaced distance from external threads 805. Suture catheter 800 may also have a relatively short distal portion 808 formed from a length of hypotube having a proximal end 810, a distal end 812 and a pattern of dog bone slits 814 laser cut along its length. The dog bone slits formed in the distal portion 808 of suture catheter 800 enable the distal portion to form tight bends while still withstanding a high degree of tension. A thin-walled stainless-steel ring 816 may be laser welded at one end to the proximal end 810 of the distal portion 808 of suture catheter 800 so that it protrudes therefrom. The distal end 806 of the proximal portion 802 of the suture catheter may then be assembled over the protruding portion of ring 816, which aligns proximal portion 802 with distal portion 808 so they can be joined together by a seam weld.

Figure 13D:
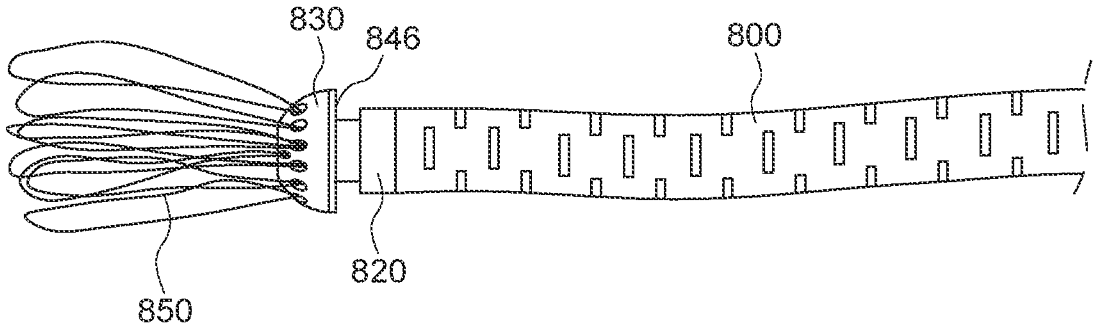
FIG. 13D is an enlarged highly schematic view of a portion of an exemplary suture catheter with a distal suture ring and a plurality of tethers attached thereto.

A proximal suture ring 820 may be laser welded to the distal end 812 of the distal portion 808 of suture catheter 800. Proximal suture ring 820 may be internally threaded at its distal end to mate with the external threads of a distal suture ring 830, shown in FIG. 13D. A plurality of tethers 850 connected to distal suture ring 830 may releasably connect to attachment features on prosthetic mitral valve 100. As a result, as suture catheter 800 is retracted relative to outer sheath 500, tension will be applied through distal suture ring 830 and tethers 850 to the prosthetic mitral valve, drawing it into the can 720 of extension catheter 700 and valve cover 550. A free-floating polytetrafluoroethylene tube 822 may be captured and held in place between proximal suture ring 820 and ring 816, lining the lumen of distal portion 808, covering any sharp edges and weld lines resulting from the assembly of the components and providing a low-friction surface to facilitate the sliding of nosecone catheter 900 within suture catheter 800. In addition, a low friction tube 824 may be heat shrunk around the outside of distal portion 808 and the spiral cut section of proximal portion 802 to reduce the friction between the outside diameter of suture catheter 800 and the inside diameter of extension catheter 700. This low friction tube may be formed from polytetrafluoroethylene or, more preferably, from a fluorinated ethylene propylene, although other low friction materials may be used.

Figure 14A:
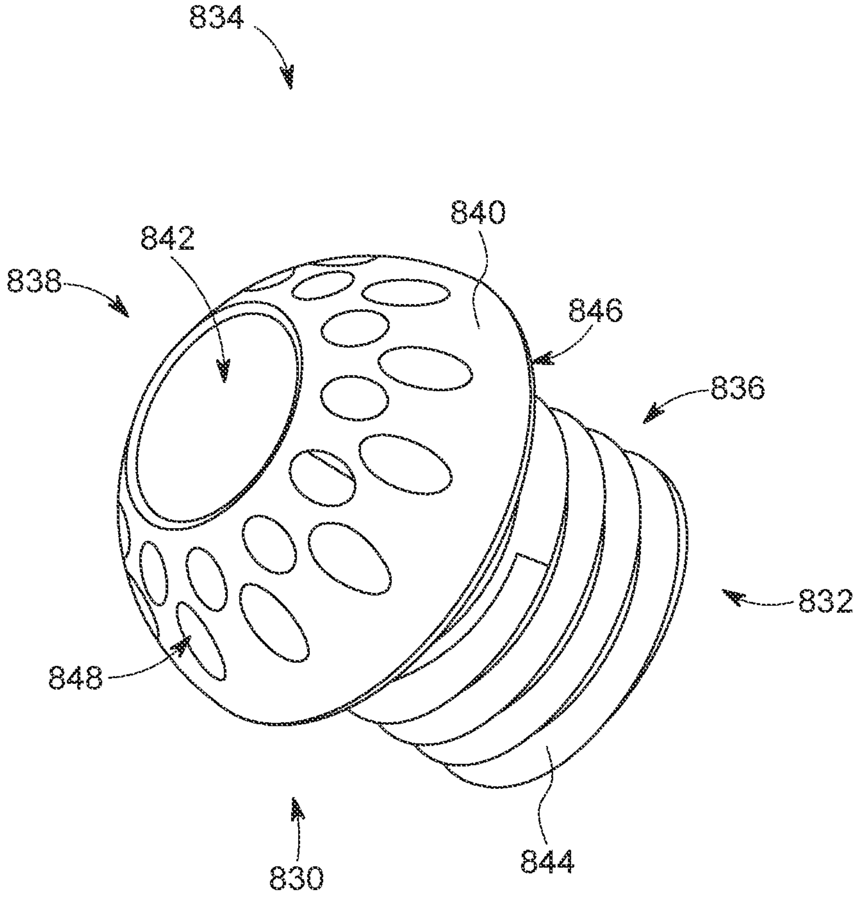
FIG. 14A is a perspective view of a distal suture ring for use with the suture catheter of FIG. 13A.

Distal suture ring 830 is connectable to the proximal suture ring 820 of suture catheter 800. A preferred distal suture ring 830 for use with catheter assembly 400 is shown in FIG. 14A and described in U.S. Provisional Application No. 63/228,269, the disclosure of which is hereby incorporated by reference herein. However, the present disclosure contemplates the use of alternative embodiments of the distal suture ring that may have a different construction and different features. Distal suture ring 830 extends in a longitudinal direction between a proximal end 832 and a distal end 834 and has somewhat of a mushroom shape with a generally cylindrical body 836 at the proximal end terminating in an enlarged head 838 with a domed or hemispherical surface 840 at the distal end. A lumen 842 may extend in the longitudinal direction through the cylindrical body 836 and head 838 of distal suture ring 830 and may be sized to receive guidewire 975 and nosecone catheter 900 therethrough. As illustrated, cylindrical body 836 may be formed with external threads 844 sized and shaped to securely connect to the internal threads in the proximal suture ring 820 of suture catheter 800. However, other mechanisms for fastening distal suture ring 830 to suture catheter 800 are also contemplated so long as they are sufficiently strong to withstand the substantial tensile forces that will be exerted thereon as prosthetic mitral valve 100 is collapsed and loaded into valve cover 550. Since the proximal suture ring/distal suture ring assembly is not bendable, it is preferable that the assembly be as short as possible in the longitudinal direction of suture catheter 800.

Figure 14B:
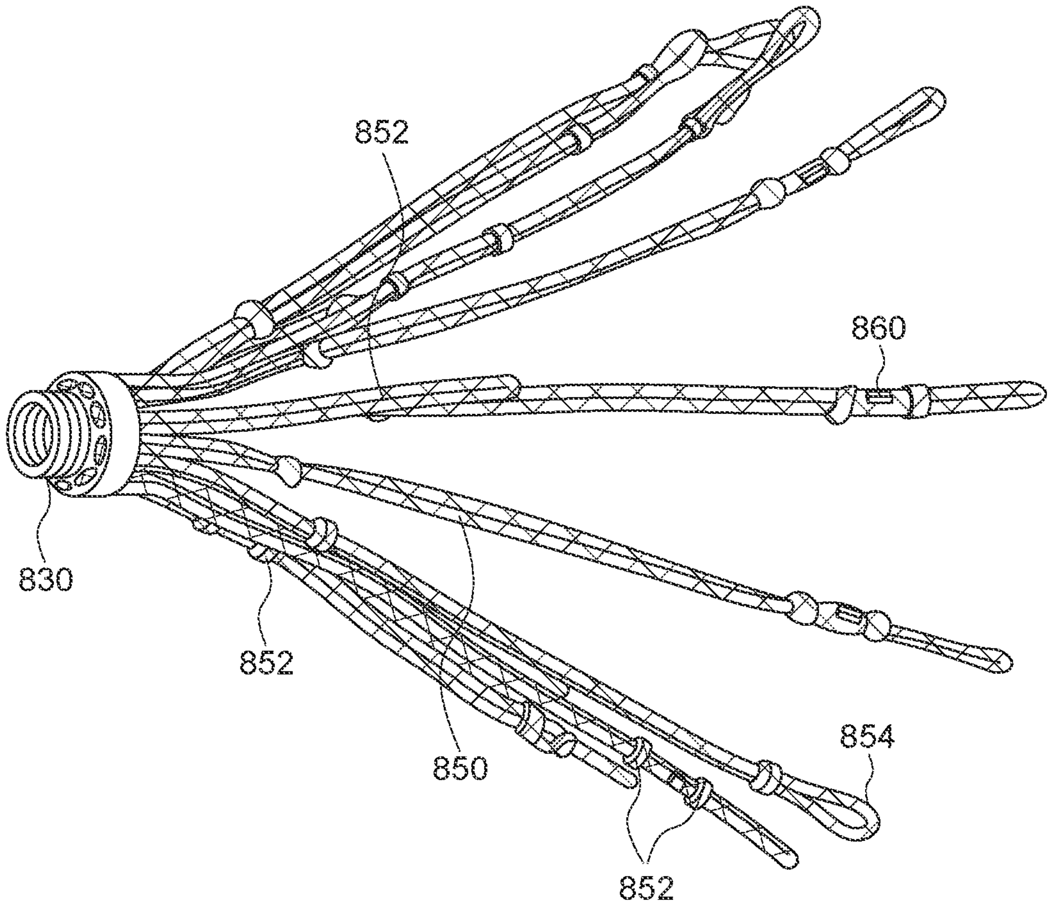
FIG. 14B is a perspective view showing tethers attached to the distal suture ring of FIG. 14A.

A plurality of round apertures or bores 848 may extend through the head 838 of distal suture ring 830 in a direction parallel to one another and parallel to the longitudinal direction of the distal suture ring, each aperture having a diameter sized to receive a length of suture thread. One or more suture threads formed of various materials, man-made and/or natural, may be attached to the head 838 of distal suture ring 830. Referring to FIG. 14B, an elongated suture thread may be threaded through a plurality of the bores 848 in distal suture ring 830 to form tethers 850. A plurality of knots 852 may be formed in tethers 850 to secure the tethers to distal suture ring 830. Knots 852 may also form a closed attachment loop 854 at the free ends of tethers 850. Attachment loops 854 are intended to releasably hook onto the pins 118 of prosthetic mitral valve 100 and to apply tension to assist in collapsing the prosthetic mitral valve during loading into valve cover 550, as described more fully below. A radiopaque marker 860 may be provided on each of tethers 850 and may be captured between a pair of knots 852.

Figure 15:
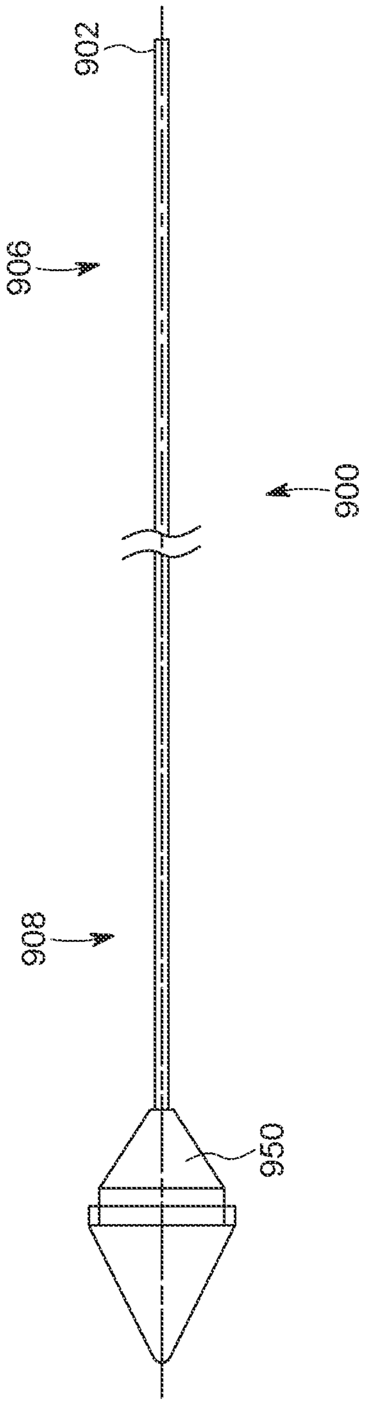
FIG. 15 is a side view of a nosecone catheter and nosecone of the catheter assembly.

Nosecone catheter 900, an embodiment of which is illustrated in FIG. 15, may be positioned within the lumen of suture catheter 800 and may comprise the innermost component of catheter assembly 400. However, the use of alternative embodiments of the nosecone catheter that may have a different construction and different features is contemplated herein. Nosecone catheter 900 has a lumen therethrough configured to receive guidewire 975. For example, the lumen of nosecone catheter 900 may have a diameter of about 0.037 inches so as to be compatible with a standard 0.035-inch guidewire, although other sizes may be utilized according to particular application needs. Nosecone catheter 900 extends from a proximal end 902 to a distal end (not shown) that resides within a nosecone 950. A proximal portion 906 of nosecone catheter 900 may be formed from a very thin-walled stainless-steel hypotube that, because of its thin wall and small diameter, is flexible. However, nosecone catheter 900 may also be formed from a polymer, such as polyimide, nylon, etc. Adjacent its distal end, nosecone catheter 900 may have a distal portion 908 that includes 2-3 concentric layers of coiled wire laser welded to the hypotube of proximal portion 906. The coiled structure of distal portion 908 provides much greater flexibility than that of proximal portion 906, enabling nosecone catheter 900 to follow the tight bends of steering catheter 600 within the restricted confines of the heart. The innermost coil of distal portion 908 may be wound in a first direction and the overlying coil may be wound in the opposite direction. In addition to providing improved flexibility, the coiled structure of distal portion 908 provides good resistance to any tension forces applied to nosecone catheter 900, thereby minimizing the possibility of the nosecone catheter breaking under such forces. To further improve the strength of distal portion 908 under tension, a third coil layer may be applied over the first two coiled layers, with the third coil layer being wound in the direction opposite that of the underlying coil layer (i.e., in the same direction as the innermost coil). Nosecone 950 may be removably attached to the distal end of nosecone catheter 900, such as by complementary threads, snap fit, bayonet connection or other known releasable connectors. By making nosecone 950 detachable from nosecone catheter 900, prosthetic mitral valve 100 can be loaded into a fully assembled catheter assembly 400, including nosecone catheter 900. That is, the distal end of nosecone catheter 900 can be inserted through prosthetic mitral valve 100 during the loading procedure, without having to slide the prosthetic mitral valve over the entire length of the nosecone catheter from its proximal end 902. Nosecone 950 may have a lumen through its length that is similar in diameter to that of the lumen through nosecone catheter 900. The lumens in nosecone 950 and nosecone catheter 900 coaxially align with one another to slidably receive guidewire 975. At least some embodiments of nosecone 950 that may be used with delivery system 200 are described in detail in U.S. Patent Publication No. 2020/0323634, the disclosure of which is hereby incorporated by reference herein.

Figure 16:
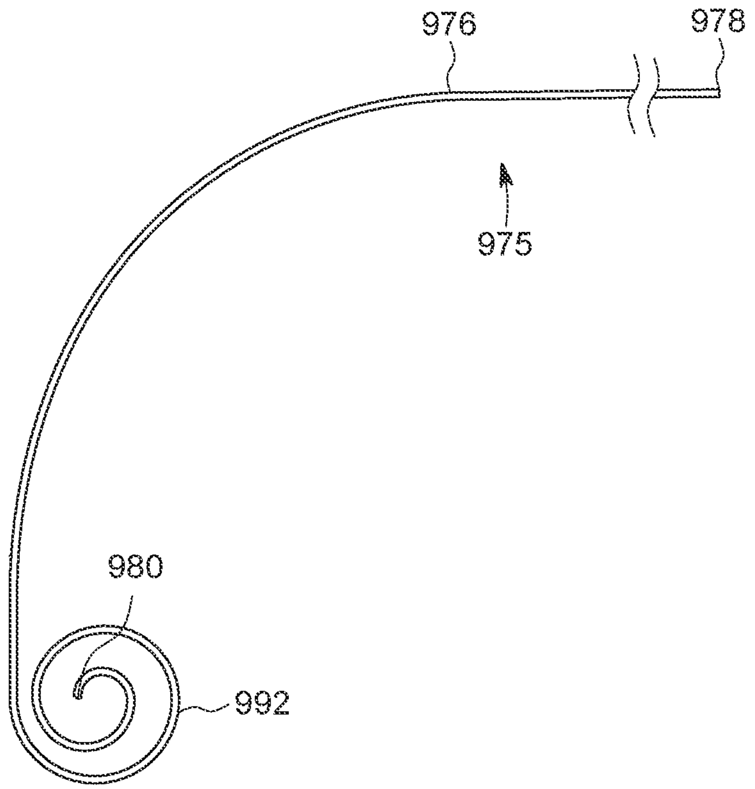
FIG. 16 is a side view of a guidewire for use with the catheter assembly, showing the pigtail distal end.

Guidewire 975 is a thin wire that is used to guide catheter assembly 400 from the insertion site in the patient to the mitral valve annulus 158 at which the prosthetic mitral valve is to be deployed. To enable catheter assembly 400 to track all the way to mitral valve annulus 158, it may be preferable for the distal tip of guidewire 975 to be advanced into left ventricle LV. Guidewire 975 preferably is formed of a superelastic material, such as nitinol, providing the guidewire with a high degree of flexibility and kink-resistance in order to accommodate the tight turns encountered while advancing from the femoral vein and inferior vena cava 150, through septum 154 and mitral valve annulus 158, to left ventricle LV. One embodiment of a guidewire 975 for use with catheter assembly 400 is shown in FIG. 16 and described in U.S. Patent Publication No. 2020/0155803, the disclosure of which is hereby incorporated by reference herein, although guidewires having different constructions may also be used. Guidewire 975 extends from a proximal end 978 to a distal end 980, and may include a distal portion 992 with a pigtail shape, as shown in FIG. 16. The curved configuration of the pigtail shape may prevent guidewire 975 from damaging cardiac or other tissue as it is advanced to left ventricle LV.

Guidewire 975 preferably has a length that is about twice the length of catheter assembly 400. Thus, for a catheter assembly that is about six feet (183 cm) long, guidewire 975 may have a length of about twelve feet (365 cm). In other embodiments, guidewire 975 may have a length of between about six feet (183 cm) and about fifteen feet (457 cm). The maximum diameter of guidewire 975 may be between about 0.014 in. and about 0.035 in. For example, guidewire 975 may have a diameter of about 0.014 in., about 0.018 in. or about 0.035 in.

Figure 17:
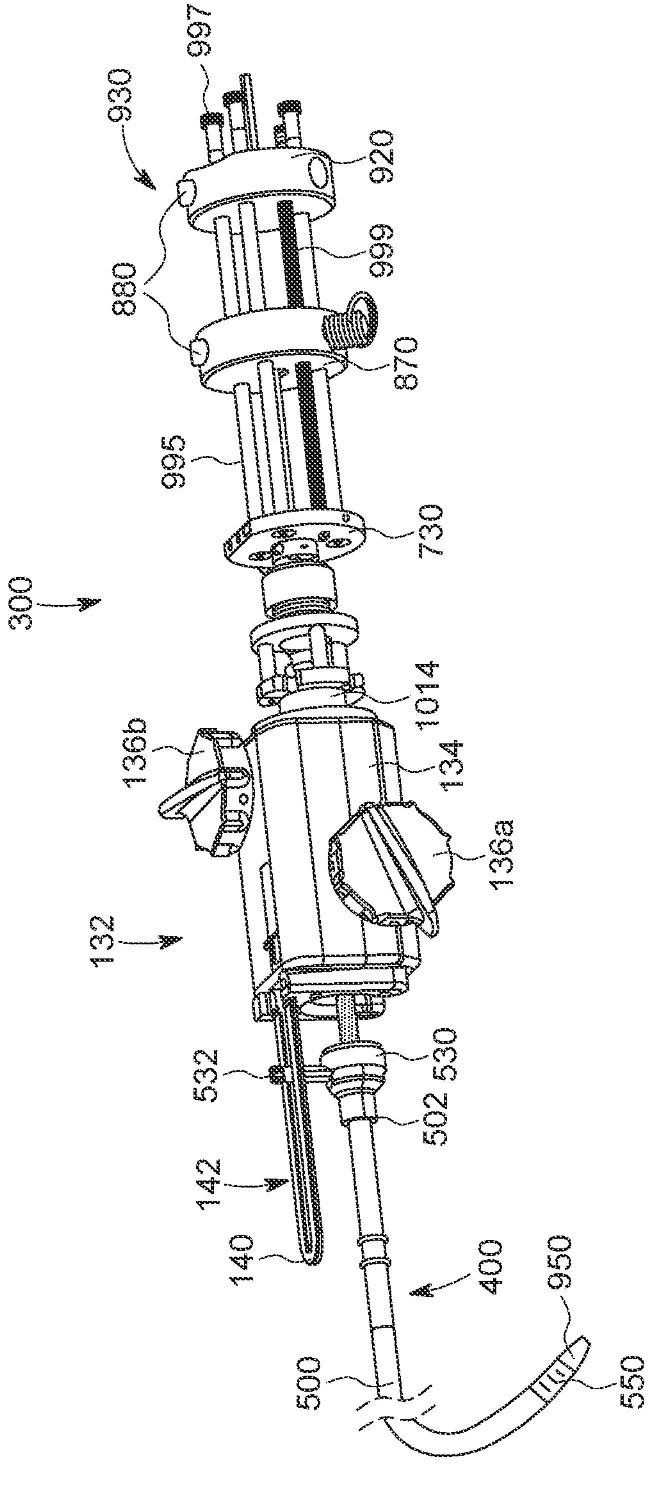
FIG. 17 is an enlarged perspective view of the delivery system shown in FIG. 2.

As mentioned previously, catheter assembly 400 is connected at its proximal end to handle assembly 300, shown in FIG. 17, which consists of steering catheter handle 132 and a series of end rings, caps and other structures, each of which may be connected at or near the proximal end of one of the components of catheter assembly 400. The proximal end 602 of steering catheter 600 may be fixedly connected to the housing 134 of steering catheter handle 132. Steering catheter handle 132 may include one or more controls **136*a*, 136*b* to which the proximal free ends of the steering catheter tension cables are connected. Manipulation of controls 136*a*, 136*b* adjusts the tension in the tension cables to deflect or straighten the distal section 612 (and, in some embodiments, the intermediate section 610) of steering catheter 600. Manipulation of one control 136*a* may deflect the distal section 612 of steering catheter 600 in a first plane, and manipulation of the other control 136*b* may deflect the distal section of the steering catheter in a plane orthogonal to the first plane, or in a plane otherwise transvers to the first plane, depending on the pattern of laser cuts in the steering catheter. Hence, controls 136*a*, 136*b* can be adjusted in tandem to position the distal end of catheter assembly 400 and valve cover 550 at a desired position and orientation relative to mitral valve annulus 158. Although controls 136*a*, 136*b* are shown in FIG. 17 as knobs, alternative embodiments may additionally or alternatively include one or more buttons, sliders, ratcheting mechanisms, or other suitable controls capable of adjusting the tension in the steering catheter tension cables to provide steering. Illustrative structures that can be used as part of steering catheter handle 132 and/or steering catheter 600 are described in U.S. Pat. No. 7,736,388, the disclosure of which is hereby incorporated by reference herein. However, it is contemplated that mechanisms that operate in a different way and that have a different structure than steering catheter handle 132 may also be used. Since steering catheter 600 is positioned within outer sheath 500**, deflection of the steering catheter causes a corresponding deflection/steering of the outer sheath.

In the embodiment shown in FIG. 17, outer sheath 500 is assembled over steering catheter 600 and extends from its distal end 504 to its proximal end 502 which, as noted above, is fixedly connected to an outer sheath hemostasis valve 530 spaced distally of steering catheter handle 132. This positioning enables outer sheath 500 to be advanced distally relative to steering catheter 600 and retracted proximally relative to the steering catheter until hemostasis valve 530 abuts steering catheter handle 132. Although the foregoing describes steering catheter handle 132 as limiting the proximal retraction of outer sheath 500, that need not be the case, and the proximal retraction of the outer sheath can be limited by other features, for example, other components of catheter assembly 400 or features of stabilizer 1000 described below. The luer lock 532 of hemostasis valve 530 extends into and is movable along an elongated slot 142 in a rigid keyway 140 fixedly connected to, and projecting distally from, steering catheter handle 132. The engagement of luer lock 532 in slot 142 also rotationally keys steering catheter 600 to outer sheath 500. As noted above, outer sheath 500 may be laser cut to produce preferred bending directions. However, the bending of outer sheath 500 relies on the bending of steering catheter 600. Accordingly, the rotational alignment of outer sheath 500 with steering catheter 600 is beneficial to the proper positioning of valve cover 550 and prosthetic mitral valve 100 relative to mitral valve annulus 158. As an alternative to the engagement of luer lock 532 within slot 142, outer sheath 500 may be rotationally aligned with and fixed relative to steering catheter 600 using any other key and corresponding keyway feature, slots and corresponding tabs, or other rotational keying mechanisms known in the art. Alternatively or additionally, alignment markers may be provided at the proximal end of catheter assembly 400 to visually indicate rotational alignment.

Extension catheter 700 extends proximally through steering catheter 600 and steering catheter handle 132 where its proximal end 702 may be fixedly coupled to an extension catheter holder 730 positioned proximally of the steering catheter handle. Extension catheter holder 730 may be in the form of a disk having a central aperture (not shown) that enables suture catheter 800 to extend proximally therethrough. A flush port (not shown) may be positioned on the rim of extension catheter holder 730 to allow flushing of the interior of extension catheter 700.

Suture catheter 800 extends proximally through extension catheter 700, steering catheter handle 132, and extension catheter holder 730 and may be fixedly coupled at its proximal end 804 to a suture catheter control 870 positioned proximally of the extension catheter holder. Suture catheter control 870 may be in the form of a disk or puck having a central aperture (not shown) through which nosecone catheter 900 may extend proximally. A flush port (not shown) may be positioned on the rim of suture catheter control 870 to allow flushing of the interior of suture catheter 800.

Nosecone catheter 900 extends proximally from nosecone 950 through suture catheter 800, steering catheter handle 132, extension catheter holder 730 and suture catheter control 870 and may be coupled to a nosecone catheter control 920. Nosecone catheter control 920 may be in the form of a disk or puck to which a proximal portion of nosecone catheter 900 may be fixedly attached. A central aperture (not shown) through nosecone catheter control 920 enables the proximal end 902 of nosecone catheter 900 and guidewire 975 to extend proximally of the nosecone catheter control. Although both suture catheter control 870 and nosecone catheter control 920 have been shown and described as disks or pucks, they may have different shapes, including spheres, ovoids, polygons or other shapes that may be grasped and translated. In addition, the shape of suture catheter control 870 may be the same as or different than the shape of nosecone catheter control 920.

Both suture catheter control 870 and nosecone catheter control 920 may be locked in longitudinal positions relative to extension catheter holder 730 or may be selectively released so that the suture catheter control is translatable proximally and distally relative to the extension catheter holder and the nosecone catheter control, and the nosecone catheter control is translatable proximally and distally relative to the extension catheter holder and the suture catheter control. In order to maintain the axial alignment of suture catheter control 870 and nosecone catheter control 920 with extension catheter holder 730 (and also the axial alignment of the components of catheter assembly 400), both the suture catheter control and the nosecone catheter control may translate along a plurality of rigid alignment rods 995. Each alignment rod 995 may be connected at its distal end to extension catheter holder 730 and may extend proximally therefrom through an aperture in suture catheter control 870 and another aperture in nosecone catheter control 920. An enlarged fitting 997 may be positioned on the free end of each alignment rod 995 to prevent nosecone catheter control 920 and suture catheter control 870 from being removed from the rods. Alignment rods 995 assure that suture catheter control 870 and nosecone catheter control 920 freely slide in the proximal and distal directions as handle assembly 300 is operated.

In some embodiments, suture catheter control 870 and/or nosecone catheter control 920 may include a release mechanism 880 that interacts with a threaded rod or lead screw 999 fixedly connected at its distal end to extension catheter holder 730 and extending proximally therefrom through the suture catheter control and nosecone catheter control. Release mechanism 880 may be biased to engage threaded rod 999, preventing suture catheter control 870 from translating proximally or distally relative to extension catheter holder 730 and nosecone catheter control 920, and preventing the nosecone catheter control from translating proximally or distally relative to the extension catheter holder and the suture catheter control. Release mechanism 880 may incorporate a spring-loaded pin, toggle release, snap shackle, quick-release skewer, set screw or another device to provide effective and rapid release from threaded rod 999. Actuating one or more of release mechanisms 880 will selectively free either suture catheter control 870 or nosecone catheter control 920, or both, to translate proximally or distally to desired positions. Moving suture catheter control 870 proximally or distally relative to nosecone catheter control 920 will selectively translate suture catheter 800 relative to nosecone catheter 900, nosecone 950 and the other components of catheter assembly 400. Moving nosecone catheter control 920 proximally or distally relative to suture catheter control 870 will selectively translate nosecone catheter 900 and nosecone 950 relative to suture catheter 800 and the other components of catheter assembly 400. Although the use of a threaded rod 999 is shown, handle assembly 300 may include a rod having other structures (grooves, divots, depressions, etc.) for engaging with release mechanisms 880 when in the engaged position.

Figure 18:
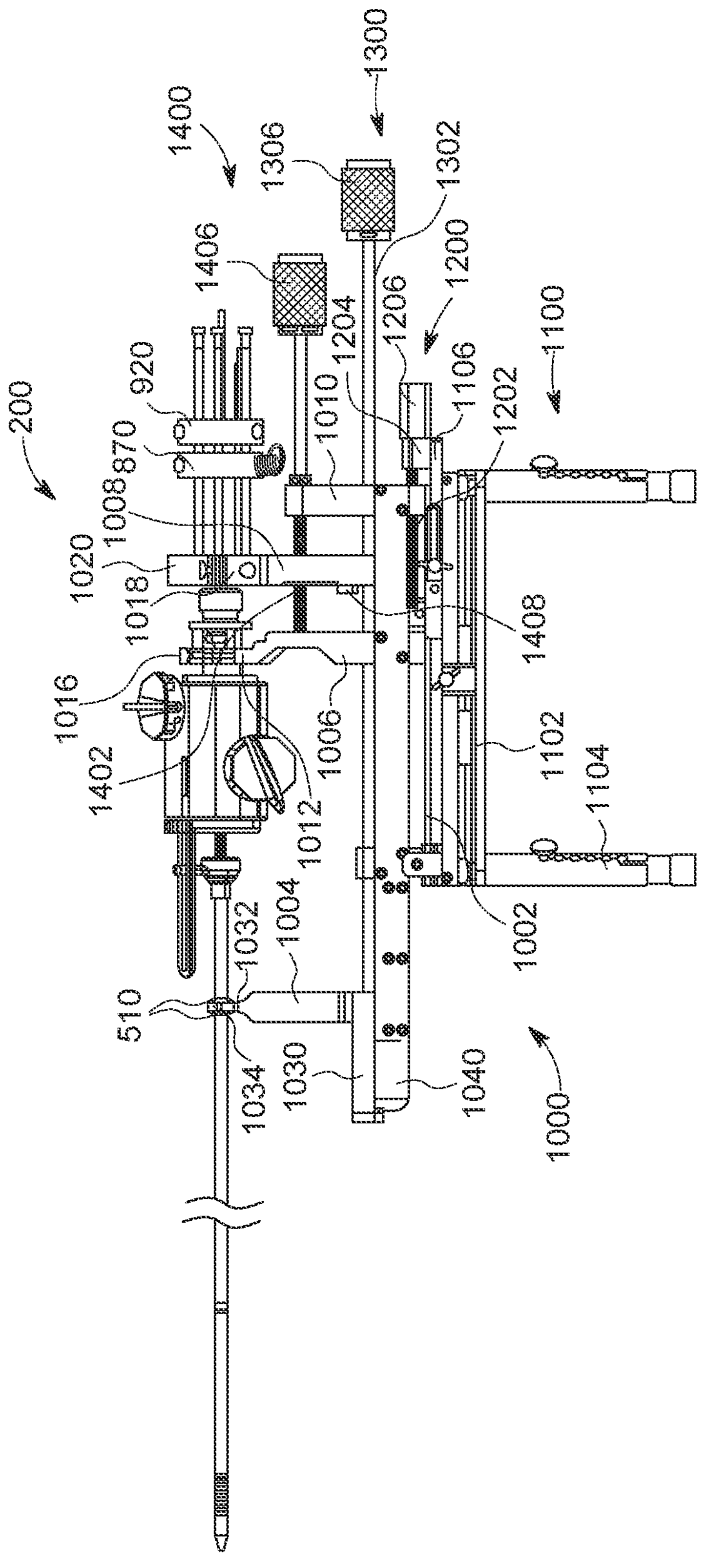
FIG. 18 is side view of the delivery system of FIG. 17 mounted to a stabilizer.

Referring to FIG. 18, delivery system 200 may be supported by a stabilizer 1000 that includes a base 1002 and a plurality of rigid supports 1004, 1006, 1008 and 1010. A handle support 1006 may be fixedly connected to base 1002 and may extend upward to a semi-circular cradle 1012 that supports a disk-shaped member 1014 (FIG. 17) connected to the proximal end of steering catheter handle 132. A cover 1016 may be assembled to cradle 1012 over disk-shaped member 1014 to secure the disk-shaped member and steering catheter handle 132 to handle support 1006. Cradle 1012 and cover 1016 together support disk-shaped member 1014 in a manner that enables steering catheter handle 132 to be rotated about its longitudinal axis in both clockwise and counterclockwise directions. Support 1010 also may be fixedly connected to base 1002 and may extend upward therefrom to a height lower than that of handle support 1006. An extension catheter support 1008 between handle support 1006 and support 1010, however, may be spaced above and translatable relative to base 1002. Extension catheter support 1008 may extend upward to a semi-circular cradle 1018 having a recess sized and shaped to receive extension catheter holder 730. A cover 1020 may be assembled to cradle 1018 over extension catheter holder 730 to secure the extension catheter holder in its assembled position.

Outer sheath support 1004 may be fixedly mounted to a slider block 1030 near the distal end of base 1002 and may extend upward to a semi-circular cradle 1032 sized to receive outer sheath 500. Cradle 1032 has a width sized to be received between two rings 510 spaced from one another around the exterior of outer sheath 500. The engagement of cradle 1032 between rings 510 prevents outer sheath 500 from translating proximally or distally relative to outer sheath support 1004. A cover 1034 may be assembled to outer sheath support 1004 over outer sheath 500 to secure the outer sheath in its assembled position. Slider block 1030 may be positioned within a channel in the top surface of a slider block guide 1040. Slider block 1030 may slide in slider block guide 1040 distally and proximally relative to base 1002 and delivery system 200 mounted thereon.

Stabilizer 1000 may be slidably mounted to a portable table 1100 that includes a platform 1102 supported by a plurality of height-adjustable legs 1104. A second platform 1106 consisting of two plates pivotally connected at one end may be mounted between platform 1102 and the base 1002 of stabilizer 1000 in a manner that enables the base to slide proximally and distally relative to table 1100 and that enables the proximal end of the base to be raised or lowered relative to platform 1102, orienting delivery system 200 at a transverse angle to horizontal.

Stabilizer 1000 also includes a plurality of actuators that selectively control the translation of base 1002 and the translation of the components of catheter assembly 400 relative to one another. Base actuator 1200 may include a threaded rod or lead screw 1202 that is engaged with internal threads in support 1010 and that also may be coupled to a support post 1204 fixedly attached to second platform 1106. The coupling of lead screw 1202 to support post 1204 is such that the lead screw is rotatable but not translatable relative to support post 1204. Rotating lead screw 1202 in one direction (via an actuating knob 1206) will cause base 1002 and all of the components assembled to the base to advance distally relative to second platform 1106 and table 1100, while rotating the lead screw in the opposite direction will cause the base and the components assembled to the base to retract proximally relative to the second platform and the table.

An outer sheath actuator 1300 includes a rod 1302, at least a distal portion of which is threaded, supported for rotation through handle support 1006, extension catheter support 1008 and support 1010. The distal end of threaded rod or lead screw 1302 is journaled for rotation in slider block 1030, and an actuating knob 1306 may be affixed to its proximal end. Lead screw 1302 rotates freely within apertures in handle support 1006 and support 1010, while being engaged with threads within extension catheter support 1008 so that the lead screw rotates but does not translate relative supports 1006 and 1010, but translates relative to support 1008. As a result, while extension catheter support 1008 is held in a fixed position, rotation of lead screw 1302 in one direction causes slider block 1030 to translate proximally, retracting outer sheath 500 relative to the other components of catheter assembly 400. Rotation of lead screw 1302 in the opposite direction causes slider block 1030 to translate distally, advancing outer sheath 500 relative to the other components of catheter assembly 400. A pair of smooth, rigid rods (not shown) may extend from slider block 1030 proximally through apertures in handle support 1006, extension catheter support 1008 and support 1010 to maintain the alignment of outer sheath support 1004 with the other portions of delivery system 200 as they translate relative to one another. The retraction of outer sheath 500 may be utilized to deploy a prosthetic heart valve held within valve cover 550 at the distal end of the outer sheath, while the advancement of the outer sheath/valve cover over the prosthetic heart valve may be utilized to recapture the valve.

Stabilizer 1000 may also include a valve positioning actuator 1400 that translates several of the components of catheter assembly 400 together relative to steering catheter 600. Positioning actuator 1400 includes a rod 1402, at least a distal portion of which is threaded. Threaded rod or lead screw 1402 is supported for rotation at its distal end in handle support 1006, extends through extension catheter support 1008, and is supported for rotation at its proximal end in support 1010. Positioning actuator 1400 is journaled in handle support 1006 and support 1010 so that it does not translate relative to those supports as it is rotated. However, lead screw 1402 is threadedly engaged with internal threads in extension catheter support 1008. As noted previously, extension catheter holder 730 is captured in the cradle 1018 in extension catheter support 1008, preventing the extension catheter holder from translating proximally or distally relative to the extension catheter support. Similarly, steering catheter handle 132 is supported by handle support 1006, which is held in a fixed position on base 1002. As a result of this arrangement, rotation of positioning actuator 1400 (via actuating knob 1406) results in the translation of extension catheter support 1008 relative to handle support 1006 and support 1010. The translation of extension catheter support 1008 results in the simultaneous translation of suture catheter control 870 and nosecone catheter control 920 by virtue of their connection to threaded rod 999, as well as the simultaneous translation of outer sheath 500 by virtue of its connection to lead screw 1302. A release mechanism 1408 may be incorporated on extension catheter support 1008 to release the extension catheter support from lead screw 1402, enabling the rapid manual translation of the extension catheter support either proximally or distally, thereby translating extension catheter holder 730, suture catheter control 870 and nosecone catheter control 920 simultaneously to either advance prosthetic mitral valve 100 relative to mitral valve annulus 158 or to retract it, possibly for re-sheathing.

In view of the forgoing connections among the various components, the rotation of positioning actuator 1400 in a first direction to translate extension catheter support 1008 simultaneously causes slider block 1030, extension catheter holder 730, suture catheter control 870 and nosecone catheter control 920 to retract proximally, while the position of steering catheter handle 132 remains fixed. Rotation of positioning actuator 1400 in the opposite direction causes the advancement in the distal direction of slider block 1030, extension catheter holder 730, suture catheter control 870 and nosecone catheter control 920, again without translating steering catheter handle 132.

As explained above, suture catheter control 870 may be translated proximally or distally relative to the other components of catheter assembly 400 by depressing release mechanism 880 and manually sliding the suture catheter control proximally or distally. Translation of suture catheter control 870 causes suture catheter 800 to translate relative to each of outer sheath 500, steering catheter 600, extension catheter 700, nosecone catheter 900 and nosecone 950. As will be explained below, the proximal retraction of suture catheter 800 relative to extension catheter 700 and/or outer sheath 500 increases the axial tension on tethers 850 to keep them connected to prosthetic mitral valve 100 and to maintain the prosthetic valve in a pre-deployed position within delivery system 200, while the distal advancement of the suture catheter relative to the extension catheter and/or the outer sheath releases the axial tension on the tethers and allows deployment of the prosthetic mitral valve.

Prosthetic mitral valve 100 may be loaded into valve cover 550 by first removing nosecone 950 from nosecone catheter 900 and flushing all of the components of catheter assembly 400 to remove air. Distal suture ring 830 with prosthetic mitral valve 100 attached to it through tethers 850 may then be assembled to proximal suture ring 820 at the distal end of suture catheter 800, and the suture catheter may be retracted to collapse the prosthetic mitral valve and draw it toward valve cover 550. A loading funnel removably attached to the distal end of valve cover 550 may assist in collapsing the valve to facilitate the loading process. Suture catheter 800 may be retracted until the tips of the atrial petals 114 of the prosthetic valve are seated in the can 720 at the distal end of extension catheter 700. Outer sheath 500 and valve cover 550 may then be advanced until prosthetic mitral valve 100 is fully positioned within the valve cover. Nosecone 950 may then be assembled to the distal end of nosecone catheter 900 and the nosecone catheter may be withdrawn until the nosecone seats against the distal end of valve cover 550. In a preferred arrangement, suture catheter 800 and tethers 850 are pretensioned after prosthetic mitral valve 100 has been loaded into valve cover 550 and prior to the insertion of catheter assembly 400 into the patient. To pretension suture catheter 800 and tethers 850, a torque wrench can be assembled to the proximal end of threaded rod 999 and the rod can be turned to retract the suture catheter relative to extension catheter 700 until a desired tension is achieved. More particularly, once the can 720 at the distal end of extension catheter 700 is seated against the tip ring 620 of steering catheter 600, any further tension applied to suture catheter 800 will be transferred to the steering catheter. Applying further tension to suture catheter 800 (through further rotation of threaded rod 999) will cause the suture catheter to lengthen slightly by the separation of the laser cuts at its distal end, creating a spring-like tension in the suture catheter. The desired tension should be within a range that is sufficient to hold prosthetic mitral valve 100 securely within can 720 at the distal end of extension catheter 700 and to maintain the connection of tethers 850 to the pins 118 on the prosthetic valve, but not so high as to significantly decrease the flexibility of the distal end of catheter assembly 400. The tension/compression relationship between suture catheter 800 and extension catheter 700 should be maintained until the atrial petals 114 of prosthetic mitral valve 100 have been released from extension catheter can 720. Delivery system 200 is now ready for delivering prosthetic mitral valve 100 into the left atrium LA of the patient and deploying the prosthetic valve in mitral valve annulus 158. Methods for preparing delivery system 200 and for loading prosthetic mitral valve 100 therein are described in more detail in U.S. Provisional Application No. 63/382,012, filed Nov. 2, 2022, the disclosure of which is hereby incorporated by reference herein.

In a conventional procedure, an incision is made in the patient's groin to access the femoral vein, and a guidewire, such as guidewire 975, is fed up through the femoral vein, advanced through the inferior vena cava 150 to the right atrium RA, through a puncture in intra-atrial septum 154 and into the left atrium LA. Catheter assembly 400 is then advanced over guidewire 975 until nosecone 950 is located in left ventricle LV and valve cover 550 is positioned in mitral valve annulus 158 such that a distal portion of prosthetic mitral valve 100 is located on the ventricular side of the annulus and a proximal portion of the prosthetic mitral valve is located on the atrial side of the annulus. Outer sheath 500 and valve cover 550 may then be partially retracted while nosecone 950 is held in place, thereby creating a separation between the nosecone and the valve cover. As valve cover 550 is retracted, it exposes the ventricular anchor 108 of prosthetic mitral valve 100, causing it to expand within left ventricle LV.

Following the release and expansion of ventricular anchor 108, outer sheath 500 and valve cover 550 may be further retracted to fully expose prosthetic mitral valve 100 (i.e., atrial anchor 106), while maintaining tension in tethers 850. Once fully exposed, prosthetic mitral valve 100 may be retracted proximally to bring the ventricular anchor into contact against the ventricular side of mitral valve annulus 158. This may be accomplished by rotating positioning actuator 1400 to retract extension catheter 700 and suture catheter 800. If extension catheter 700 is already in a fully retracted position, ventricular anchor 108 may be brought into contact with the ventricular side of mitral valve annulus 158 by rotating prosthetic mitral valve 100. This may be done by rotating steering catheter handle 132 in the posterior direction. The rotation of steering catheter handle 132 will cause the simultaneous rotation of outer sheath 500 and valve cover 550 by virtue of the engagement of the luer lock 532 of hemostasis valve 530 within the slot 142 in rigid keyway 140. As a result of the bends at the distal end of catheter assembly 400, rotating steering catheter handle 132 and valve cover 550 will cause prosthetic mitral valve 100 to pivot relative to the plane of mitral valve annulus 158 until ventricular anchor 108 contacts the mitral valve annulus. Ventricular anchor 108 will deflect as it contacts mitral valve annulus 158, enabling prosthetic mitral valve 100 to move closer to its proper orientation relative to the valve annulus, with atrial anchor 106 on the atrial side of mitral valve annulus 158.

At this point, prosthetic mitral valve 100 may still be held by tethers 850 in a not yet fully deployed condition, with atrial anchor 106 still held in a collapsed condition within the can 720 of extension catheter 700. Since leaflets 113 are not yet functioning when ventricular anchor 108 is retracted against mitral valve annulus 158, the positioning of the ventricular anchor will impede the flow of blood from left atrium LA to left ventricle LV. Therefore, as ventricular anchor 108 is retracted against mitral valve annulus 158, it is desirable to simultaneously advance suture catheter 800 to release atrial anchor 106 so that blood can begin flowing through the prosthetic valve. This may be accomplished by actuating release mechanism 1408 to quickly retract extension catheter support 1008 and extension catheter 700, drawing ventricular anchor 108 against the mitral valve annulus and, at the same time, actuating release mechanism 880 to translate suture catheter control 870 and suture catheter 800 distally to relieve the tension in tethers 850, enabling atrial anchor 106 to expand and release from can 720. Upon its expansion, atrial anchor 106 will contact the atrial side of mitral valve annulus 158, thus sandwiching the mitral valve annulus between the atrial anchor and the ventricular anchor and securing prosthetic mitral valve 100 in place. After prosthetic mitral valve 100 has been detached from suture catheter 800, the suture catheter may be retracted, pulling tethers 850 back into extension catheter 700. Nosecone catheter 900 may then be retracted proximally until nosecone 950 is seated against the distal end of valve cover 550, and catheter assembly 400 may be removed from the patient.

During the deployment of prosthetic mitral valve 100 from valve cover 550, the limited space within human heart H will require the distal end of steering catheter 600 to be sharply bent in one or more likely two planes to properly position the prosthetic valve relative to mitral valve annulus 158. In order to be able to retract valve cover 550 over the sharp bends of steering catheter 600, the valve cover is laser cut to form cuts 552 and slits 554, as described above. These cuts and slits are formed in a way that defines a pair of spines (not shown) along the length of valve cover 550 that are strong enough to withstand the unsheathing forces while still providing the valve cover with sufficient flexibility to follow the sharp bends of the steering catheter. For valve cover 550 to be able to follow the sharp bends of steering catheter 600, it is necessary for the bending plane of the valve cover to be aligned with the most distal bending plane of the steering catheter. If the bending planes of steering catheter 600 and valve cover 550 are not aligned, there is a substantial risk that the valve cover will break as the user attempts to retract the valve cover to deploy prosthetic mitral valve 100. As noted previously, the capture of the luer lock 532 of hemostasis valve 530 within the slot 142 in the rigid keyway 140 attached to steering catheter handle 132 assures that outer sheath 500, and thus valve cover 550, remains rotationally fixed relative to the steering catheter handle, and thus steering catheter 600. This alignment will enable valve cover 550 to be retracted to deploy the ventricular anchor 108 of prosthetic mitral valve 100.

If the deployed ventricular anchor 108 is too deep and extension catheter 700 cannot be retracted (i.e., it is already in a fully retracted position), ventricular anchor 108 may be lifted into contact with the ventricular side of mitral valve annulus 158 by rotating steering catheter 600. The object of this procedure is to have ventricular anchor/ventricular disk 108 contact mitral valve annulus 158 and deflect, enabling the prosthetic mitral valve to move closer to its proper position and orientation relative to the valve annulus. This may be accomplished by rotating steering catheter handle 132 in the posterior direction. The engagement of luer lock 532 in the slot 142 in rigid keyway 140 will cause outer sheath 500 and valve cover 550 to rotate along with steering catheter handle 132. Further rotation of outer sheath 500 and valve cover 550 will be inhibited once ventricular anchor 108 of prosthetic mitral valve 100 contacts mitral valve annulus 158, such that continued rotation of steering catheter handle 132 will cause steering catheter 600 to begin to twist relative to the outer sheath. As a result, outer sheath 500 and steering catheter 600 will become misaligned, which has the potential to break valve cover 550.

The following will describe several alternative embodiments of a coupling mechanism that will maintain the rotational alignment of outer sheath 500 and valve cover 550 with steering catheter 600 up to and through the deployment of ventricular anchor 108, but following the deployment of the ventricular anchor will permit the outer sheath to rotate freely relative to the steering catheter and steering catheter handle 132. In describing these embodiments, elements that are the same as those in delivery system 200 described above have the same reference number, while elements that are different follow the reference number with a letter A, B or C, depending on the embodiment of the coupling mechanism being described.

Figure 19:
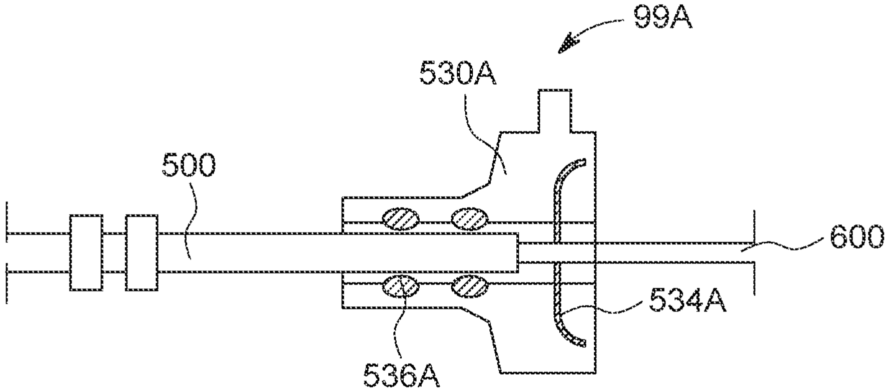
FIG. 19 is an enlarged, highly schematic longitudinal cross-section of the proximal end of the outer sheath showing an embodiment of a coupling mechanism for releasably coupling rotation of the delivery device handle to the outer sheath.

A first such alternative embodiment of the coupling mechanism is coupling mechanism 99A shown in the enlarged cross-sectional view of FIG. 19. Coupling mechanism 99A is similar to the coupling mechanism coupling hemostasis valve 530 to outer sheath 500 in delivery system 200 described above. However, rather than fixedly connecting the hemostasis valve to outer shaft 500, such as by adhesive, as in delivery system 200, the hemostasis valve 530A of coupling mechanism 99A is connected to the outer sheath so that it is able to rotate relative to the outer sheath when the amount of torque applied to the outer sheath exceeds a certain threshold. As shown in FIG. 19, in addition to the silicon seal 534A typically found in a hemostasis valve, hemostasis valve 530A includes one or more O-rings 536A interposed between the hemostasis valve and outer sheath 500, creating a fluid-tight seal that will prevent the infiltration of air during the flushing of catheter assembly 400. O-rings 536A can be sized to create a sufficient amount of friction with outer sheath 500 that the outer sheath will remain aligned with steering catheter 600 until the torque exerted on hemostasis valve 530A by rotation of steering catheter handle 132 exceeds a threshold amount. This threshold amount can be adjusted by controlling the amount by which O-rings 536A are compressed between outer sheath 500 and hemostasis valve 530A. Once this threshold amount of torque is exceeded, the continued rotation of steering catheter handle 132 will enable steering catheter 600 and hemostasis valve 530A to rotate without rotating outer sheath 500 or not rotating the outer sheath by the same amount, thereby avoiding the excessive forces that can break valve cover 550.

Figure 20:
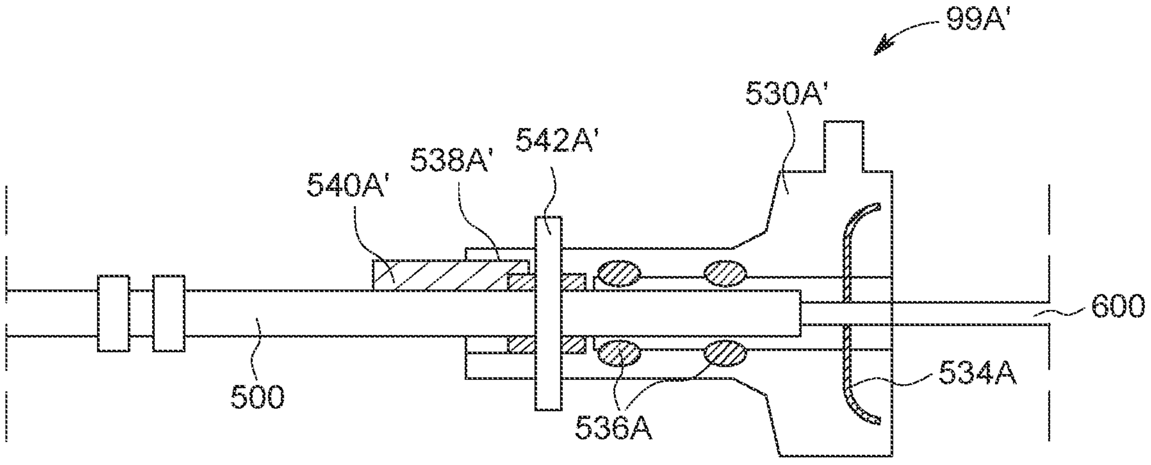
FIG. 20 is an enlarged, highly schematic longitudinal cross-section showing a variant of the coupling mechanism shown in FIG. 19.

In a variant of the foregoing embodiment, rather than rely on overcoming the friction between O-rings 536A and outer sheath 500, a keying mechanism that can be removed or deactivated as needed can be provided between the outer sheath and the hemostasis valve. Such variant is illustrated in the enlarged cross-sectional view of FIG. 20. In the coupling mechanism 99A' according to this variant, hemostasis valve 530A' is similar to hemostasis valve 530A, and includes a silicon seal 534A and one or more O-rings 536A interposed between the hemostasis valve and outer sheath 500. Hemostasis valve 530A' also includes a recess 538A' formed in its the distal end. Recess 538A' is sized to receive a block or key 540A' welded or otherwise connected to outer sheath 500 in a fixed position distal to hemostasis valve 530A' and parallel to the elongation direction of the outer sheath. Recess 538A' acts as a keyway such that, when key 540A' is engaged in the keyway, they prevent the rotation of outer sheath 500 relative to hemostasis valve 430A' and steering catheter 600. That is, during the advancement of catheter assembly 400 to a target site in the patient and the deployment of the ventricular anchor 108 of prosthetic mitral valve 100, key 540A' will be nested within recess 538A' to maintain the alignment of outer sheath 500 with steering catheter 600. However, when it is desired to rotate steering catheter handle 132 to move ventricular anchor 108 into contact with mitral valve annulus 158, hemostasis valve 530A' can be pulled back slightly in a proximal direction until key 540A' is no longer engaged in recess 538A', enabling the hemostasis valve to rotate without rotating outer sheath 500. As a result, continued rotation of steering catheter handle 132 once ventricular anchor 108 has contacted mitral valve annulus 158 will not create excessive forces that could potentially break valve cover 550. To prevent hemostasis valve 530A' from inadvertently moving proximally and disengaging key 540A' from recess 538A' prior to the deployment of ventricular anchor 108, the hemostasis valve may be provided with a spring clip 542A'. Spring clip 542A' can engage a groove (not shown) in the outer circumference of outer sheath 500 to prevent hemostasis valve 530A' from translating relative to the outer sheath. When it is desired to release outer sheath 500 from the rotation of steering catheter handle 132, spring clip 542A' can be removed and hemostasis valve 530A' can be retracted until key 540A' is no longer engaged in recess 538A'.

Figure 21:
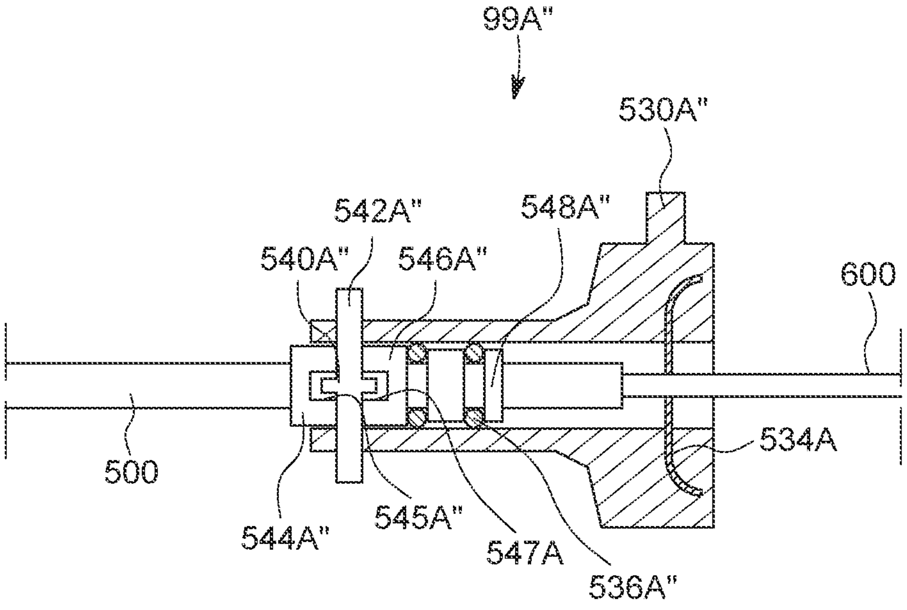
FIG. 21 is an enlarged, highly schematic longitudinal cross-section showing a variant of the coupling mechanism of FIG. 20.

One disadvantage of the use of the keying mechanism described above is the need to retract hemostasis valve 530A' proximally to remove key 540A' from recess 538A' and enable outer sheath 500 to rotate freely relative to hemostasis valve 530A' and steering catheter handle 132. This disadvantage can be eliminated by attaching the key directly to the spring clip. A coupling mechanism 99A" having a hemostasis valve 530A" incorporating this modification is shown in FIG. 21. Hemostasis valve 530A" is similar to hemostasis valve 530A', and includes a silicon seal 534A and one or more O-rings 536A interposed between the hemostasis valve and outer sheath 500. A ring 544A" may be welded or otherwise fixedly connected around the exterior of outer sheath 500 at a position within hemostasis valve 530A". Ring 544A" has a pocket 545A" that faces toward spring clip 542A". Spring clip 542A" can engage a groove (not shown) in the outer circumference of outer sheath 500 to prevent hemostasis valve 530A" from translating relative to the outer sheath. Optionally, a second ring 546A" may be welded or otherwise fixedly connected around the exterior of outer sheath 500 at a position within hemostasis valve 530A". Ring 546A" has a pocket 547A" that faces toward spring clip 542A" and toward the pocket 545A" in ring 544A". A key 540A" may be fixedly connected to spring clip 542A" such that it is oriented in a direction parallel to the elongation direction of outer sheath 500. Rather than fixedly attach a separate key 540A" to spring clip 542A", the wire forming the spring clip may be bent in a way that integrally forms the key or a similarly effective structure. In either case, key 540A" is sized to reside within pocket 545A" and, when present, pocket 547A". When both ring 544A" and ring 546A" are attached to outer sheath 500, the groove in the outer sheath may be eliminated as the engagement of key 540A" within pockets 545A" and pocket 547A" will prevent hemostasis valve 530A" from translating relative to the outer sheath. When it is desired to rotate steering catheter handle 132 to move ventricular anchor 108 into contact with mitral valve annulus 158, spring clip 542A" can be removed, simultaneously removing key 540A" from pocket 545A" (and pocket 547A"), thereby enabling outer sheath 500 to rotate freely relative to hemostasis valve 530A" and the steering catheter handle. Thus, in this variant, retraction of the hemostasis valve is not necessary to enable free rotation of outer sheath 500 relative to the hemostasis valve and the steering catheter handle.

In each of the variants of coupling mechanisms 99A described above (with the exception of the variant shown in FIG. 21), O-rings 536A are held in place by recesses formed in the interior of hemostasis valve 530A. These recesses are difficult to form during the injection molding of the hemostasis valve. The hemostasis valve variant shown in FIG. 21 overcomes this difficulty. Hemostasis valve 530A" is formed with a smooth, uninterrupted interior surface. To hold O-rings 536A in place, two rings 548A" may be connected, such as by laser welding, at spaced locations on the exterior of outer sheath 500. Rings 548A" define pockets which securely hold O-rings 536A in place.

Figure 22:
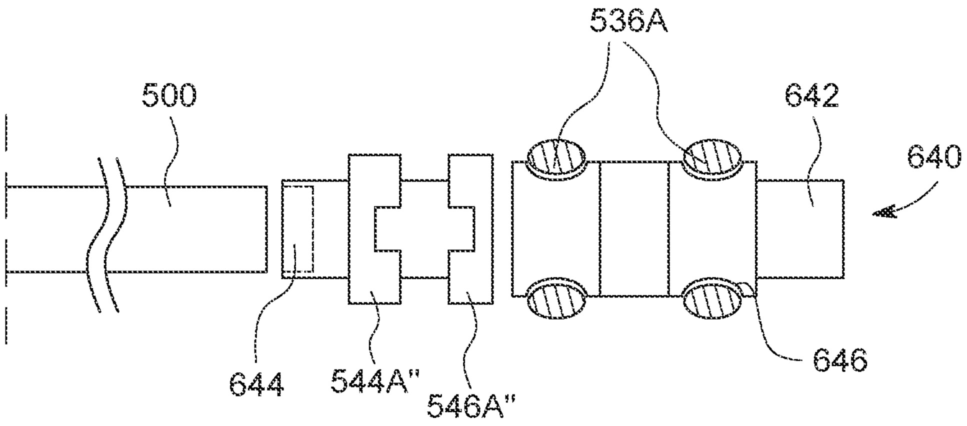
FIG. 22 is an enlarged side view of an adapter for use with the coupling mechanism shown in FIG. 21.

Rather than attach multiple rings to the exterior of outer sheath 500, a single adapter may be formed incorporating rings 544A" and 546A", as well as surfaces for retaining O-rings 536A. One potential embodiment of such an adapter 640 is shown in FIG. 22. Adapter 640 may be in the form of a length of a rigid tube 642, such as a stainless-steel hypotube, that is milled at its distal end to form a pocket 644 sized to receive the proximal end of outer sheath 500 to a depth sufficient to ensure the alignment of the adapter with the outer sheath. Rings 544A" and 546A" can be fixedly secured to tube 642, such as by laser welding (or a larger diameter tube can be machined to form rings 544A" and 546A"), so that they are appropriately spaced apart to receive key 540A". Proximally of ring 546A", adapter 640 may be machined with a pair of curved recesses 646 spaced apart from one another, or may be fitted with rings incorporating such spaced recesses. Recesses 646 are sized to receive O-rings 536A and hold them securely in place. Once assembled, adapter 640 has an outer diameter sized to be receivable within hemostasis valve 530A". As adapter 640 includes all of the functions of the embodiment shown in FIG. 21, the proximal end of outer sheath 500 may simply be inserted into pocket 644 and fixed in place, such as by laser welding, to complete the assembly. In an alternative arrangement, adapter 640 may be injection molded from a rigid polymer with all of the features described above, and the adapter may be glued to the proximal end of outer sheath 500. A delivery system incorporating the coupling mechanism according to this embodiment would operate in the same way as the embodiment of FIG. 21 described above.

Figure 23:
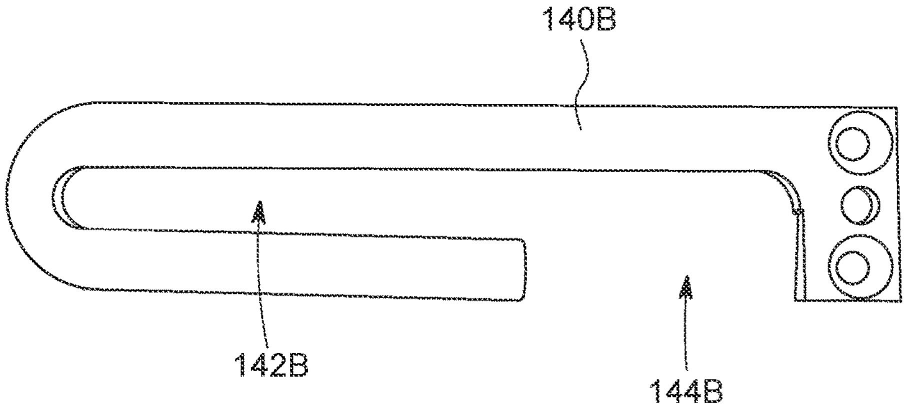
FIG. 23 is an enlarged top view of a keyway according to another embodiment.
Figure 24:
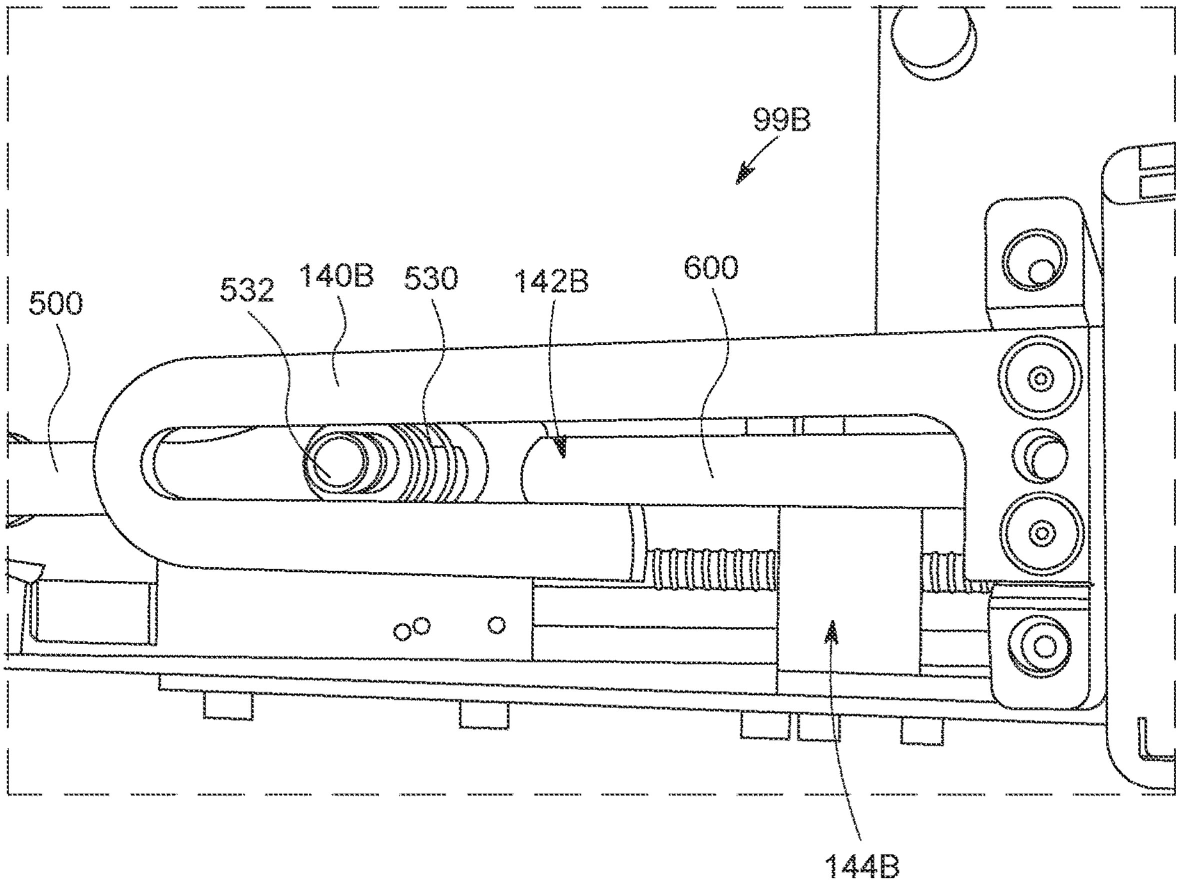
FIG. 24 is a top view of a coupling mechanism incorporating the keyway shown in FIG. 23.
Figure 25A:
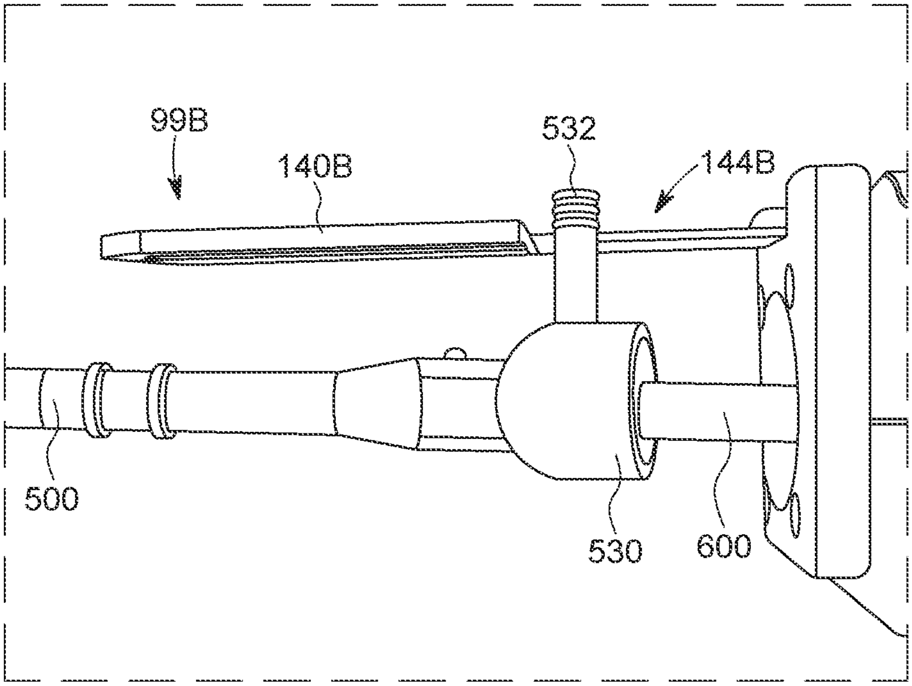
FIGS. 25A-C are side views illustrating the rotation of the coupling mechanism shown in FIG. 24.
Figure 25B:
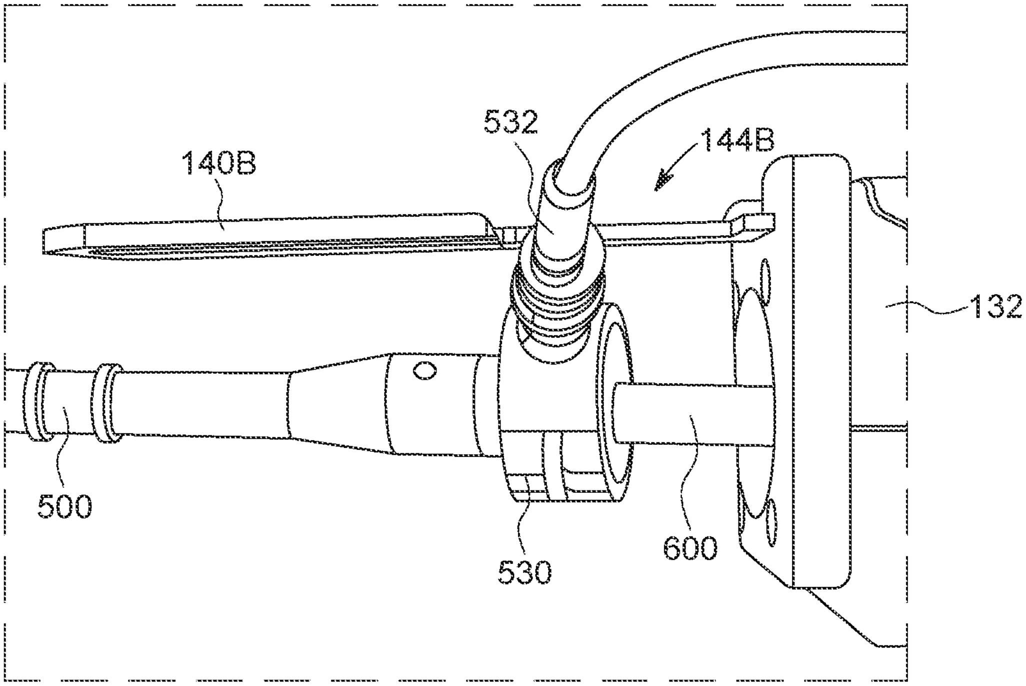
Figure 25C:
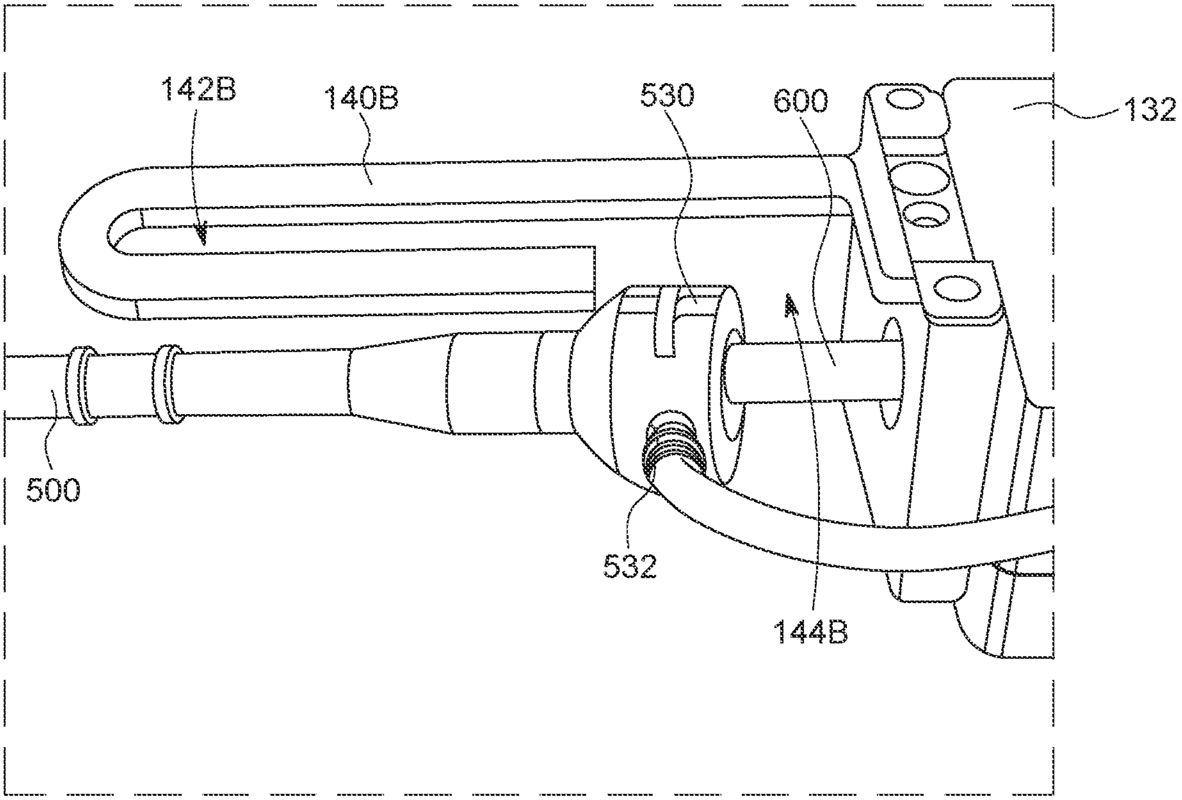

A coupling mechanism 99B according to another embodiment is shown in FIGS. 23-25. In the embodiments of coupling mechanism 99B described below, hemostasis valve 530 is fixedly connected to outer shaft 500, such as by adhesive. A rigid keyway 140B for use in coupling mechanism 99B is shown in FIG. 23. Rather than forming a slot that is entirely enclosed, such as slot 142 in keyway 140 described above, a proximal portion of one leg of keyway 140B has been eliminated, leaving a gap 144B such that the slot 142B is not entirely enclosed, enabling hemostasis valve 530 to exit the keyway as steering catheter handle 132 is rotated in the posterior (clockwise) direction. More particularly, at the beginning of a deployment procedure, the luer lock 532 of hemostasis valve 530 is positioned at the distal end of the slot 142B in keyway 140B, as shown in FIG. 24. In this position, outer sheath 500 is fully advanced such that the distal end of valve cover 550 contacts nosecone 950, and the outer sheath is also rotationally aligned with steering catheter 600 to ensure that the distal end of the outer sheath (and the valve cover) bends in the direction of the most distal bend in the steering catheter. Following the retraction of valve cover 550 and the deployment of the ventricular anchor 108 of prosthetic mitral valve 100, luer lock 532 will be positioned more proximally in slot 142B, alongside the gap 144B in keyway 140B, as shown in FIG. 25A. When steering catheter handle 132 is rotated in the posterior (clockwise) direction to seat ventricular anchor 108 against mitral valve annulus 158, keyway 140B will rotate along with the steering catheter handle, but the gap 144B in the keyway will enable hemostasis valve 530 and outer sheath 500 to remain in place as luer lock 532 exits slot 142B, as shown in FIGS. 25B and C. As a result, once ventricular anchor 108 is seated against mitral valve annulus 158, it will be possible to continue rotating steering catheter handle 132 without rotating outer sheath 500, such that excessive forces will not be created at the distal end of the outer sheath that could potentially break valve cover 550.

Figure 26A:
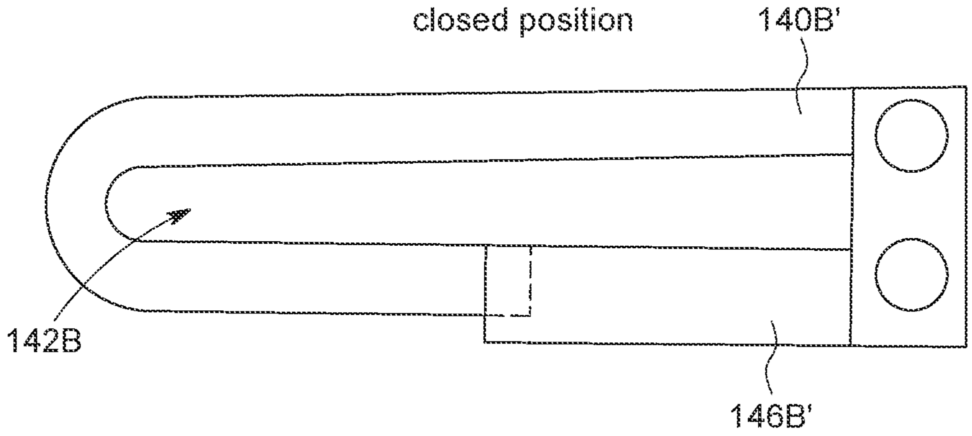
FIG. 26A is a top view of a variant of the keyway of FIG. 23 in a closed condition.
Figure 26B:
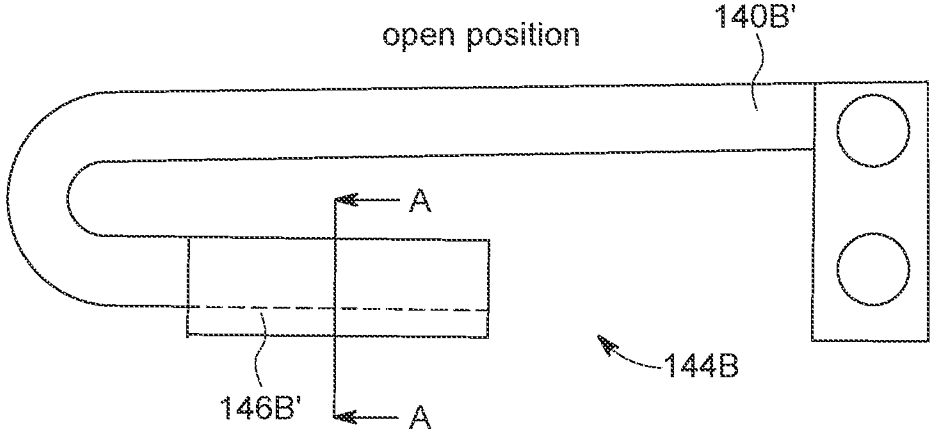
FIG. 26B is a top view of the keyway of FIG. 26A in an open condition.
Figure 26C:
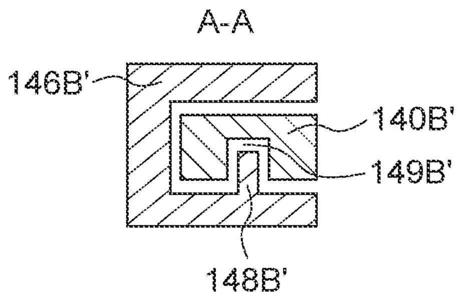
FIG. 26C is a transverse cross-section of the keyway of FIG. 26A taken along section lines A-A of FIG. 26B.

Variants of keyway 140B can enable slot 142B to be entirely closed during the advancement of catheter assembly 400 to the target site and the deployment of ventricular anchor 108, but to then be opened to expose gap 144B when it is desired to rotate steering catheter handle 132 and seat the ventricular anchor against mitral valve annulus 158. One such variant is keyway 140B' shown in FIGS. 26A-C. Keyway 140B' is substantially identical to keyway 140B, but includes a leg segment 146B' that is slidable to close gap 144B. FIG. 26A shows leg segment 146B' in a closed position with its proximal end butting against the proximal portion of keyway 140B'. This closed position will keep luer lock 532 trapped in slot 142B (and outer sheath 500 rotationally aligned with steering catheter 600) as catheter assembly 400 is advanced to the target site and ventricular anchor 108 is deployed, even if steering catheter handle 132 is inadvertently rotated when luer lock 532 is positioned at the proximal end of slot 142B adjacent gap 144B. When it is desired to seat ventricular anchor 108 against mitral valve annulus 158, leg segment 146B' can be slid distally to the open position shown in FIG. 26B, exposing gap 144B and enabling luer lock 532 to exit slot 142B as steering catheter handle 132 and steering catheter 600 are rotated, while hemostasis valve 530 and outer sheath 500 remain stationary. To keep leg segment 146B' aligned with keyway 140B' in the closed position and to provide the keyway with a smooth surface against which luer lock 532 may slide, the leg segment may be provided with a longitudinal rib 148B' that is slidable within a longitudinal channel 149B' in keyway 140B', as shown in FIG. 26C. Alternatively, rib 148B' may be provided in keyway 140B' and channel 149B' may be provided in leg segment 146B'.

Figure 27A:
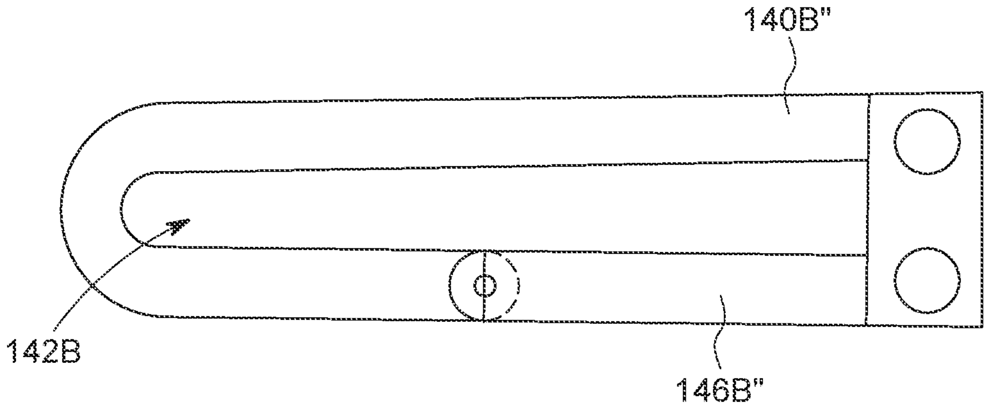
FIG. 27A is a top view of another variant to the keyway of FIG. 23 in a closed condition.
Figure 27B:
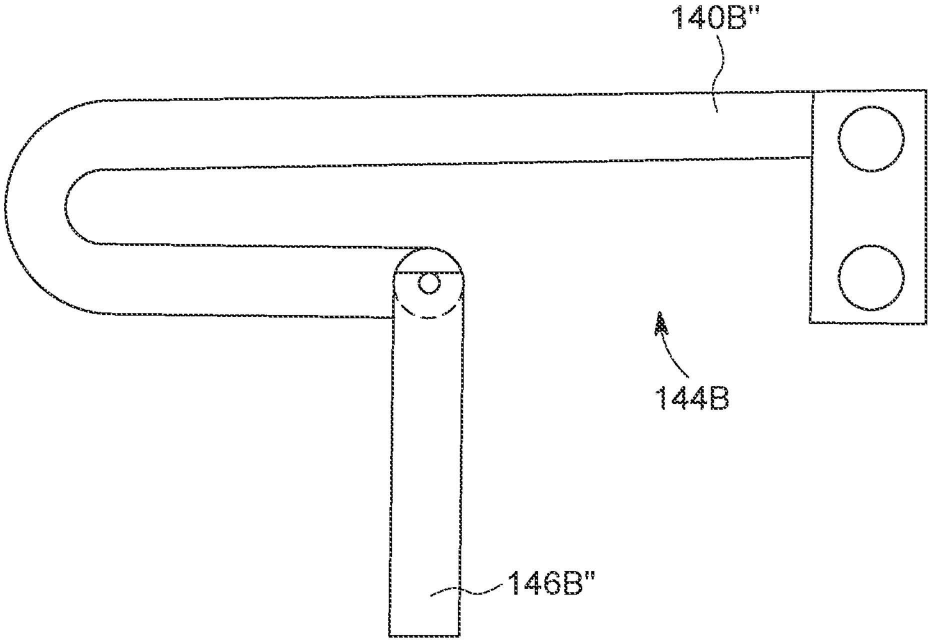
FIG. 27B is a top view of the keyway of FIG. 27A in an open condition.

Another keyway variant that can enable slot 142B to initially be entirely closed and subsequently opened to expose gap 144B is keyway 140B" shown in FIGS. 27A-B. Keyway 140B" is substantially identical to keyway 140B', and includes slot 142B and gap 144B. However, rather than leg segment 146B' that is slidable relative to the remainder of keyway 140B', keyway 140B" includes a leg segment 146B" that is pivotable relative to the remainder of the keyway. That is, one end of leg segment 146B" is pivotably attached to keyway 140B" and can be moved between the closed condition shown in FIG. 27A and the open condition shown in FIG. 27B. The closed position will keep luer lock 532 trapped in slot 142B (and outer sheath 500 rotationally aligned with steering catheter 600) as catheter assembly 400 is advanced to the target site and ventricular anchor 108 is deployed, even if steering catheter handle 132 is inadvertently rotated when hemostasis valve 530 is adjacent gap 144B. When ventricular anchor 108 is to be seated against mitral valve annulus 158, leg segment 146B" can be pivoted to the open position shown in FIG. 27B, exposing gap 144B and enabling luer lock 532 to exit slot 142B as steering catheter handle 132 and steering catheter 600 are rotated, while hemostasis valve 530 and outer sheath 500 remain stationary.

Figure 27C:
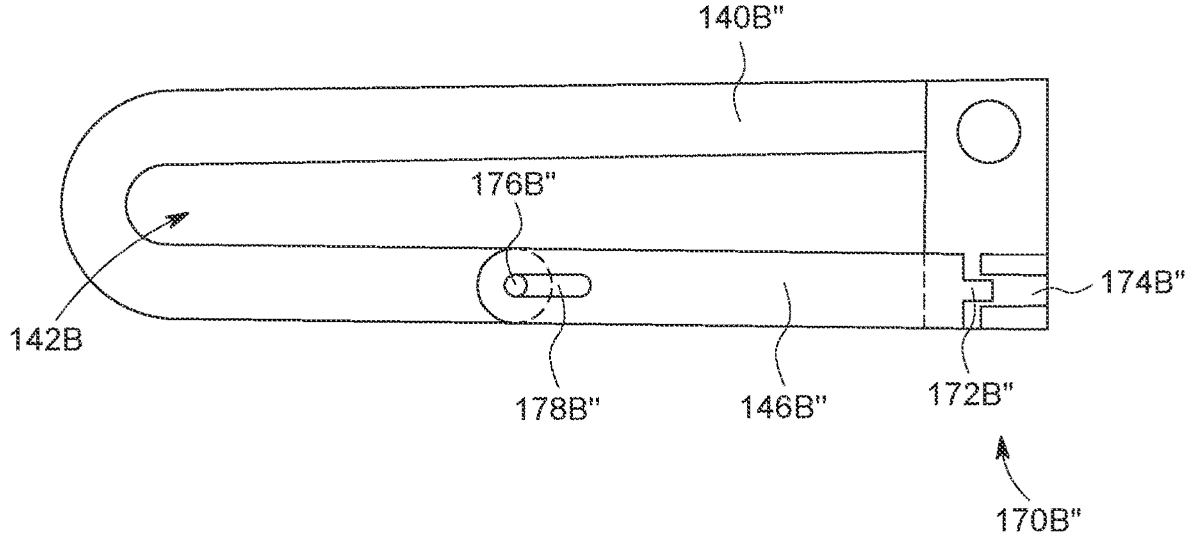
FIG. 27C is a top view of a variant of the keyway of FIG. 27A in the closed condition and incorporating a locking mechanism.

To prevent leg segment 146B" from inadvertently moving to the open position before full deployment of ventricular anchor 108, keyway 140B" may include a locking mechanism 170B", one embodiment of which is shown in FIG. 27C. Locking mechanism 170B" includes a boss 172B" protruding from the free end of leg segment 146B" and sized to be received in a recess 174B" formed in an opposing section of keyway 140B" when in the locked condition. It will be appreciated that the positions of boss 172B" and recess 174B" may be reversed. At its other end, leg segment 146B" may be attached to keyway 140B" by a pin 176B" that extends through the keyway and through an elongated slot 178B" in the leg segment. Elongated slot 178B" enables leg segment 146B" to slide distally relative to keyway 140B" by an amount sufficient for boss 172B" to slide out from recess 174B" so that the leg segment may be pivoted to the open condition. It will be appreciated that other mechanisms known to those skilled in the art may be used for locking leg segment 146B" in the closed condition. It will also be appreciated that rather than pivoting laterally between the open and closed conditions, leg segments similar to leg segment 146B" may be connected to keyway 140B" so that they pivot upwards and/or downwards relative to the plane of the keyway to move between the open and closed conditions.

Figure 28:
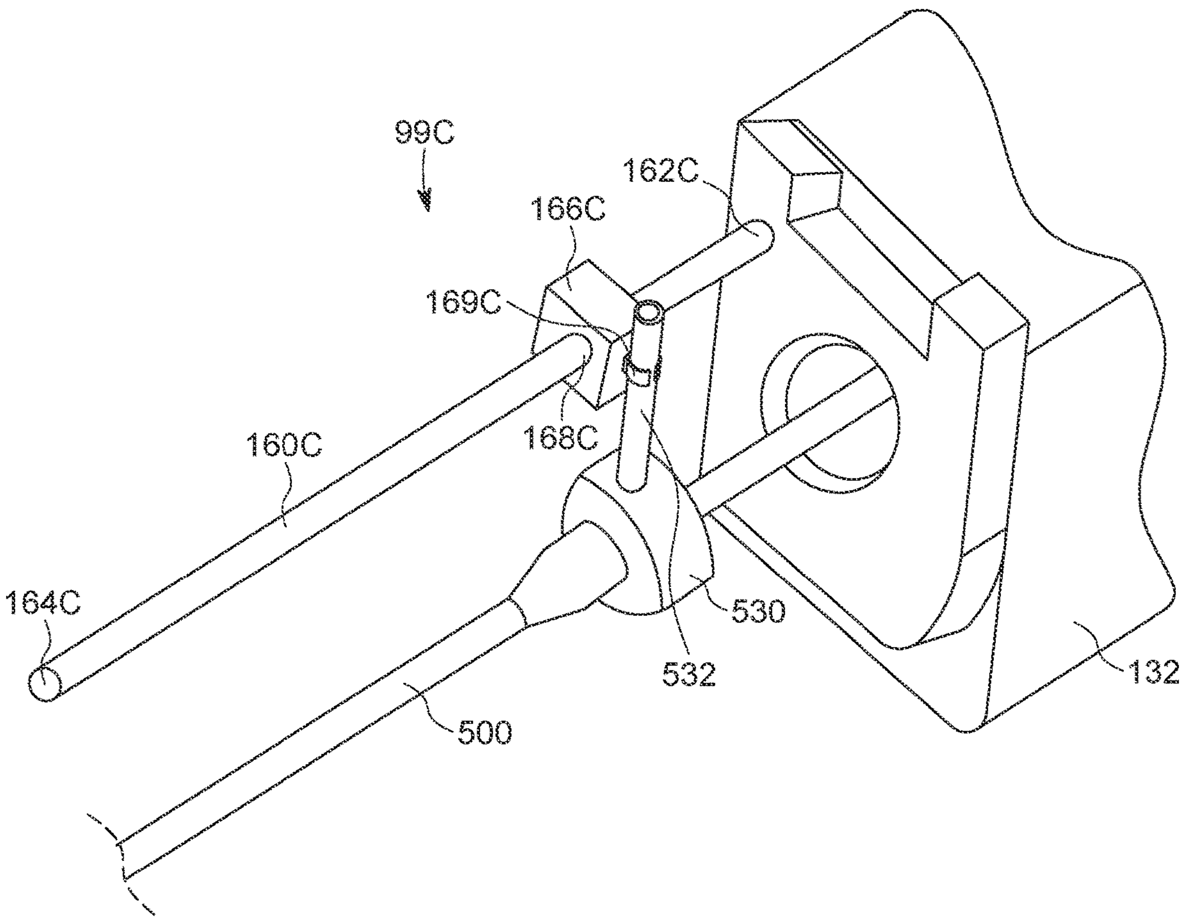
FIG. 28 is a perspective view of a coupling mechanism according to another embodiment.
Figure 29:
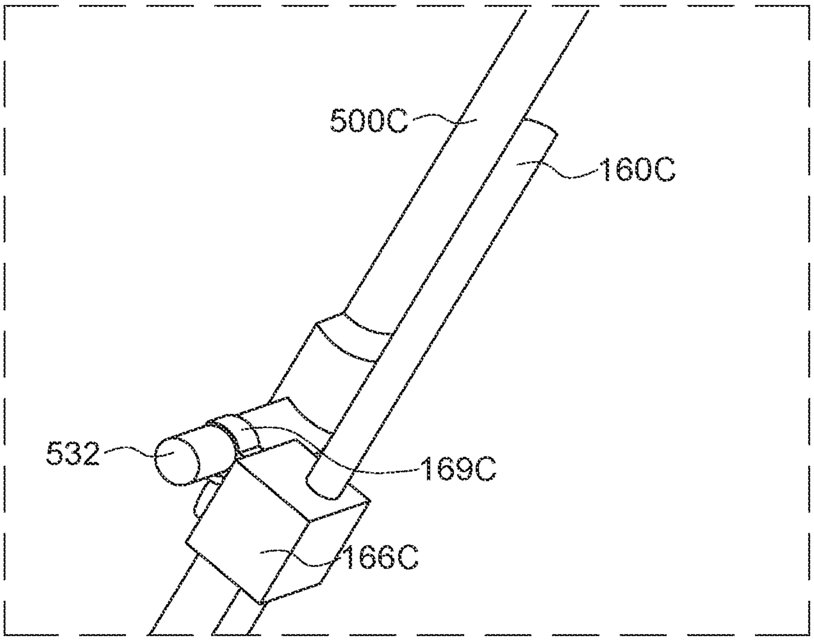
FIG. 29 is an enlarged perspective view showing the rider attached to the hemostasis valve in the coupled condition.
Figure 30C:
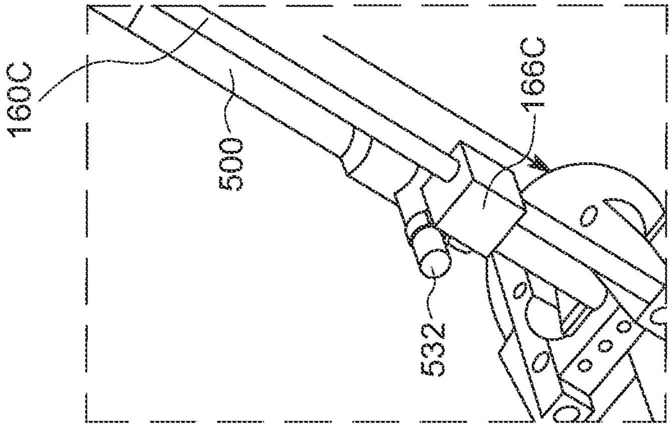
FIGS. 30A-C are enlarged perspective views showing the movement of the rider along with the outer sheath during the initial stage of deployment of the prosthetic mitral valve.
Figure 30B:
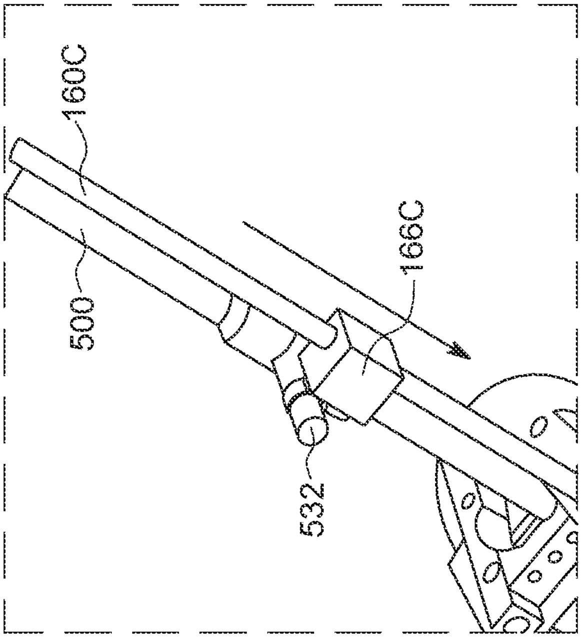

A coupling mechanism 99C according to another embodiment is shown in FIGS. 28-30. Coupling mechanism 99C differs from the coupling mechanisms described above in that it eliminates keyway 140 entirely and replaces it with a cylindrical rod 160C formed from a rigid material, such as stainless-steel. Referring to FIG. 28, rod 160C is connected at a proximal end 162C to steering catheter handle 132, and extends distally therefrom in a direction parallel to outer sheath 500 to a free end 164C. A generally square or rectangular rider 166C has a cylindrical bore 168C therethrough for slidably mounting the rider to rod 160C. Rider 166C is preferably made from a polymer having a low coefficient of friction, such as polyoxymethylene, polytetrafluoroethylene, and the like, so that it does not bind as it travels along rod 160C. Rider 166C may also be formed from a metal, preferably a metal that is softer than stainless-steel, for example brass, so that the rider does not bind as it travels along rod 160C. In yet another alternative, rider 166C may be formed from stainless-steel or another hard metal with the addition of a sliding element, such as a low coefficient of friction polymer bushing or ball bearings, interposed between the rider and rod 160C. Although rod 160C is described as cylindrical, that need not be the case, and the rod can have a cross-section of any shape, including elliptical, rectangular, triangular and the like, as long as the bore 168C through rider 166C has a corresponding shape or another shape capable of securely receiving the rod. Also, although rider 166C has been described as square or rectangular, that need not be the case. Rider 166C may have any shape of a size sufficient to slidably mount to rod 160C and to securely hold a clip 169C. As shown in FIG. 29, clip 169C is fixedly connected to rider 166C and releasably connected to the luer lock 532 of hemostasis valve 530. Clip 169C can be of any type of releasable connector, as long as it is capable of securely but releasably connecting rider 166C to luer lock 532. In one embodiment, clip 169C may have a pair of resilient arms that encircle luer lock 532 partially, but not completely. When subjected to a force tending to pull clip 169C away from luer lock 532, the arms will separate from one another, releasing the clip from the luer lock. Other types of releasable clips can include bayonet connectors, ball and socket connectors, magnetic connectors, and the like.

Figure 30A:
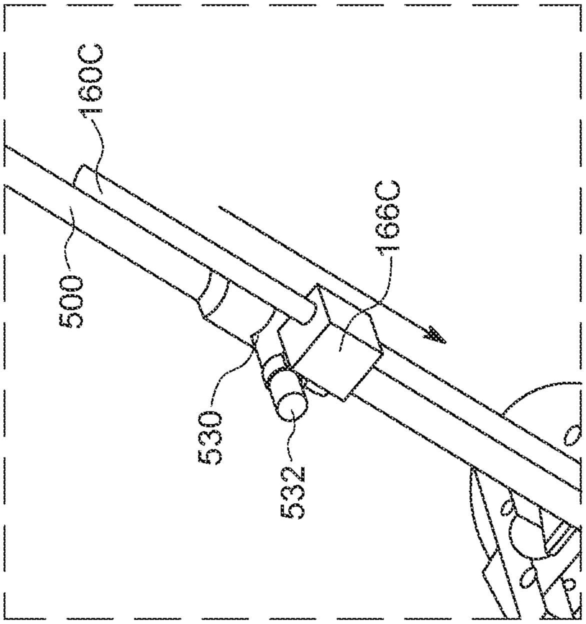

At the start of a procedure to implant prosthetic mitral valve 100 into a patient, outer sheath 500 will be at a fully advanced position with valve cover 550 contacting nosecone 950. Hemostasis valve 530 with luer lock 532 will be at a relatively distal position, as shown in FIG. 30A, and rider 166C will be positioned adjacent the hemostasis valve with clip 169C attached to the luer lock. To deploy the ventricular anchor 108 of prosthetic mitral valve 100, outer sheath 500 is retracted, as shown by the arrows in FIGS. 30B and 30C. Since hemostasis valve 530 is fixedly connected to the proximal end of outer sheath 500, the retraction of the outer sheath will result in the simultaneous retraction of the hemostasis valve. As clip 169C connects rider 166C to luer lock 532, the rider will also retract, maintaining its position adjacent hemostasis valve 530. As a result, rider 166C will prevent outer sheath 500 from rotating, thereby maintaining the alignment of the distal end of the outer sheath and valve cover 550 with steering catheter 600. After ventricular anchor 108 has been deployed, steering catheter handle 132 may be rotated in the posterior (clockwise) direction to lift the ventricular anchor into contact with the ventricular side of mitral valve annulus 158. Since rod 160C is fixedly connected to steering catheter handle 132, the rotation of the steering catheter handle will similarly rotate the rod and rider 166C in a direction away from outer sheath 500. However, the complex bends at the distal end of outer sheath 500 will prevent it from rotating to the same extent as steering catheter handle 132, creating tension in clip 169C. When that tension exceeds the amount of clamping force exerted by clip 169C on luer lock 532, the clip will disconnect from the luer lock, enabling steering catheter 600 to rotate without rotating outer sheath 500 or not rotating the outer sheath by the same amount, thereby avoiding the excessive forces that can break valve cover 550. The amount of clamping force exerted on luer lock 532 by clip 169C can be adjusted in several ways, including altering the height and/or thickness of the clip, altering the amount by which the clip encircles the luer lock, or forming the clip with a material having a greater or lesser Shore hardness. It should be noted that coupling mechanism 99C releases in a passive manner. That is, coupling mechanism 99C will release without any positive action on the part of the operator of the delivery system. This is advantageous in that the operator could potentially forget to actively release other coupling mechanisms during the stress of the implantation procedure, such that rotating steering catheter 600 to lift prosthetic mitral valve 100 against the mitral valve annulus could result in damage to valve cover 550 and an inability to fully release the prosthetic valve.

To summarize the foregoing, one embodiment of a delivery system for delivering a medical device to a targeted anatomical site within a patient has been described. The delivery system includes a catheter assembly, including an outer sheath extending in a longitudinal direction between a proximal end and a distal end; a connecting arm connected to the outer sheath at the proximal end, the connecting arm extending away from the outer sheath in a direction transverse to the longitudinal direction; a valve cover at the distal end of the outer sheath, the valve cover having a proximal end, a distal end, and a size and a shape for housing the medical device in a collapsed condition; and a steering catheter coaxially arranged within the outer sheath, the steering catheter having a longitudinal axis and a flexible distal portion capable of deflecting in multiple directions relative to the longitudinal axis, wherein deflection of the distal portion of the steering catheter causes a corresponding deflection of a distal portion of the outer sheath. The delivery system also includes a handle connected to the steering catheter such that rotation of the handle causes a corresponding rotation of the steering catheter about the longitudinal axis; and a coupling mechanism having a first condition in which the outer sheath is rotationally coupled to the steering catheter so that rotation of the steering catheter about the longitudinal axis results in a corresponding rotation of the outer sheath, the coupling mechanism having a second condition in which the outer sheath is rotationally uncoupled from the steering catheter so that rotation of the steering catheter about the longitudinal axis does not result in a corresponding rotation of the outer sheath; and/or the coupling mechanism may include a rigid keyway overlapping a proximal portion of the outer sheath and having a first end fixedly connected to the handle and a second end, the rigid keyway having an elongated slot extending in the longitudinal direction, the slot being sized to receive the connecting arm so that the connecting arm is able to move in the longitudinal direction within the slot; and/or the coupling mechanism may further include a plurality of O-rings interposed between the connecting arm and the outer sheath, the O-rings frictionally connecting the connecting arm to the outer sheath; and/or rotation of the handle may create a torsional force between the steering catheter and the outer sheath, the coupling mechanism being in the first condition when the torsional force is less than a frictional force between the steering catheter and the outer sheath so that the outer sheath is rotationally coupled to the steering catheter, and the coupling mechanism being in the second condition when the torsional force is greater than the frictional force between the steering catheter and the outer sheath so that the outer sheath is rotationally uncoupled from the steering catheter; and/or the connecting arm may be slidable in the longitudinal direction relative to the outer sheath, the coupling mechanism may include a key fixedly connected to the outer sheath and a recess in the connecting arm sized to receive the key, the coupling mechanism may be in the first condition when the key is positioned in the recess so that the outer sheath is rotationally coupled to the steering catheter, and the coupling mechanism may be in the second condition when the connecting arm is slid away from the key until the key is no longer in the recess so that the outer sheath is rotationally uncoupled from the steering catheter; and/or the outer sheath may include a circumferential slot and the coupling mechanism may include a clip having a connected condition coupled to the connecting arm and received in the slot to prevent the connecting arm from sliding relative to the outer sheath and a released condition removed from the connecting arm and from the slot to enable the connecting arm to slide relative to the outer sheath;

the outer sheath may include a recess, the coupling mechanism may include a clip and a key connected to the clip, the clip having a connected condition coupled to the conning arm with the key positioned in the recess and a released condition removed from the connecting arm so that the key is not in the recess, the coupling mechanism may be in the first condition when the clip is in the connected condition so that the outer sheath is rotationally coupled to the steering catheter, and the coupling mechanism may be in the second condition when the clip is in the released condition so that the outer sheath is rotationally uncoupled from the steering catheter; and/or the coupling mechanism may include an adapter and a clip, the adapter may include a tubular portion having a length direction and an internal diameter at one end sized to receive a proximal end of the outer sheath, at least one ring on the tubular portion defining a recess on an exterior portion of the tubular portion and extending in the length direction, and a plurality of additional rings spaced apart on the tubular portion and defining spaces for retaining O-rings on the tubular portion; and the clip may include a key connected to the clip, the clip having a connected condition coupled to the conning arm with the key positioned in the recess and a released condition removed from the connecting arm so that the key is not in the recess; and/or the rigid keyway may have a first leg extending in the longitudinal direction on one side of the slot and a second leg extending in the longitudinal direction on another side of the slot, the keyway defining a gap between the second leg and the handle, the connecting arm being positioned in the slot between the first leg and the second leg in the first condition of the coupling mechanism so that rotation of the steering catheter in a first direction about the longitudinal axis results in a corresponding rotation of the outer sheath, and the connecting arm being positioned between the first leg and the gap in the second condition of the coupling mechanism so that rotation of the steering catheter in the first direction about the longitudinal axis causes the connecting arm to leave the slot and does not result in a corresponding rotation of the outer sheath; and/or the rigid keyway may include a leg segment movable between an open position and a closed position, the leg segment in the closed position filling the gap so that the slot is closed from the first end of the rigid keyway to the second end of the rigid keyway and rotation of the steering catheter in the first direction about the longitudinal axis does not cause the connecting arm to leave the slot, and the leg segment in the open position exposing the gap so that rotation of the steering catheter in the first direction about the longitudinal axis causes the connecting arm to leave the slot; and/or the leg segment may be slidable relative to the second leg between the open position and the closed position; and/or the leg segment may be pivotable relative to the second leg between the open position and the closed position; and/or the rigid keyway may include a locking mechanism for releasably locking the leg segment in the closed position. delivery system for delivering a medical device to a targeted anatomical site within a patient Another embodiment of a delivery system for delivering a medical device to a targeted anatomical site within a patient has also been described. The delivery system includes a catheter assembly, including an outer sheath extending in a longitudinal direction between a proximal end and a distal end; a connecting arm connected to the outer sheath at the proximal end, the connecting arm extending away from the outer sheath in a direction transverse to the longitudinal direction; a valve cover at the distal end of the outer sheath, the valve cover having a proximal end, a distal end, and a size and a shape for housing the medical device in a collapsed condition; and a steering catheter coaxially arranged within the outer sheath, the steering catheter having a longitudinal axis and a flexible distal portion capable of deflecting in multiple directions relative to the longitudinal axis, wherein deflection of the distal portion of the steering catheter causes a corresponding deflection of a distal portion of the outer sheath. The delivery system also includes a handle connected to the steering catheter such that rotation of the handle causes a corresponding rotation of the steering catheter about the longitudinal axis; and a coupling mechanism. The coupling mechanism includes a rigid rod having a proximal end fixedly connected to the handle and extending in the longitudinal direction to a distal end, a rider slidably mounted on the rod, and a clip releasably connecting the rider to the connecting arm. The coupling mechanism has a first condition in which the rider is connected to the connecting arm so that rotation of the steering catheter about the longitudinal axis results in a corresponding rotation of the outer sheath, and the coupling mechanism has a second condition in which the rider is released from the connecting arm so that rotation of the steering catheter about the longitudinal axis does not result in a corresponding rotation of the outer sheath; and/or the clip may include first and second arms that together partially encircle the rod; and/or the clip may be fixedly connected to the rider and releasably connected to the connecting arm.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A delivery system for delivering a prosthetic heart valve to a targeted anatomical site within a patient, the delivery system comprising:

a catheter assembly, including:

an outer sheath extending in a longitudinal direction between a proximal end and a distal end;

a hemostasis valve connected to the outer sheath at the proximal end, the hemostasis valve including a connecting arm extending away from the outer sheath in a direction transverse to the longitudinal direction;

a valve cover at the distal end of the outer sheath, the valve cover having a proximal end, a distal end, and a size and a shape for housing the prosthetic heart valve in a collapsed condition; and a steering catheter coaxially arranged within the outer sheath, the steering catheter having a longitudinal axis and a flexible distal portion capable of deflecting in multiple directions relative to the longitudinal axis, wherein deflection of the distal portion of the steering catheter causes a corresponding deflection of a distal portion of the outer sheath;

a handle connected to the steering catheter such that rotation of the handle causes a corresponding rotation of the steering catheter about the longitudinal axis;

a coupling mechanism having a first condition in which the outer sheath is rotationally coupled to the steering catheter so that rotation of the steering catheter about the longitudinal axis results in a corresponding rotation of the outer sheath, the coupling mechanism having a second condition in which the outer sheath is rotationally uncoupled from the steering catheter so that rotation of the steering catheter about the longitudinal axis does not result in a corresponding rotation of the outer sheath; and a rigid keyway overlapping a proximal portion of the outer sheath and having a first end fixedly connected to the handle and a second end, the rigid keyway having an elongated slot extending in the longitudinal direction, the slot being sized to receive the connecting arm so that the connecting arm is slidable in the longitudinal direction within the slot.

2. The delivery system as claimed in claim 1, wherein the coupling mechanism further includes a plurality of O-rings interposed between the hemostasis valve and the outer sheath, the O-rings frictionally connecting the hemostasis valve to the outer sheath.

3. The delivery system as claimed in claim 2, wherein rotation of the handle creates a torsional force between the steering catheter and the outer sheath, the coupling mechanism is in the first condition when the torsional force is less than a frictional force between the steering catheter and the outer sheath so that the outer sheath is rotationally coupled to the steering catheter, and the coupling mechanism is in the second condition when the torsional force is greater than the frictional force between the steering catheter and the outer sheath so that the outer sheath is rotationally uncoupled from the steering catheter.

4. The delivery system as claimed in claim 1, wherein the coupling mechanism includes a key fixedly connected to the outer sheath and a recess in the hemostasis valve sized to receive the key, the coupling mechanism is in the first condition when the key is positioned in the recess so that the outer sheath is rotationally coupled to the steering catheter, and the coupling mechanism is in the second condition when the connecting arm is slid away from the key until the key is no longer in the recess so that the outer sheath is rotationally uncoupled from the steering catheter.

5. The delivery system as claimed in claim 4, wherein the outer sheath includes a circumferential slot and the coupling mechanism includes a clip having a connected condition coupled to the hemostasis valve and received in the slot to prevent the connecting arm from sliding relative to the outer sheath and a released condition removed from the connecting arm and from the slot to enable the connecting arm to slide relative to the outer sheath.

6. The delivery system as claimed in claim 1, wherein the coupling mechanism includes an adapter and a clip, the adapter including:

a tubular portion having a length direction and an internal diameter at one end sized to receive a proximal end of the outer sheath;

at least one ring on the tubular portion defining a recess on an exterior portion of the tubular portion and extending in the length direction; and a plurality of additional rings spaced apart on the tubular portion and defining spaces for retaining O-rings on the tubular portion; and the clip including a key connected to the clip, the clip having a connected condition coupled to the hemostasis valve with the key positioned in the recess and a released condition removed from the hemostasis valve so that the key is not in the recess.

7. The delivery system as claimed in claim 1, wherein the rigid keyway has a first leg extending in the longitudinal direction on one side of the elongated slot and a second leg extending in the longitudinal direction on another side of the elongated slot, the keyway defining a gap between the second leg and the handle, the connecting arm being positioned in the slot between the first leg and the second leg in the first condition of the coupling mechanism so that rotation of the steering catheter in a first direction about the longitudinal axis results in a corresponding rotation of the outer sheath, and the connecting arm being positioned between the first leg and the gap in the second condition of the coupling mechanism so that rotation of the steering catheter in the first direction about the longitudinal axis causes the connecting arm to leave the slot and does not result in a corresponding rotation of the outer sheath.

8. The delivery system as claimed in claim 7, wherein the rigid keyway includes a leg segment movable between an open position and a closed position, the leg segment in the closed position filling the gap so that the slot is closed from the first end of the rigid keyway to the second end of the rigid keyway and rotation of the steering catheter in the first direction about the longitudinal axis does not cause the connecting arm to leave the slot, and the leg segment in the open position exposing the gap so that rotation of the steering catheter in the first direction about the longitudinal axis causes the connecting arm to leave the slot.

9. The delivery system as claimed in claim 8, wherein the leg segment is slidable relative to the second leg between the open position and the closed position.

10. The delivery system as claimed in claim 8, wherein the leg segment is pivotable relative to the second leg between the open position and the closed position.

11. The delivery system as claimed in claim 8, wherein the rigid keyway includes a locking mechanism for releasably locking the leg segment in the closed position.

* * * * *